United States Patent
Taylor et al.

(10) Patent No.: US 11,315,660 B2
(45) Date of Patent: Apr. 26, 2022

(54) METHOD OF DETECTING AND TREATING ENDOMETRIOSIS IN A FEMALE SUBJECT

(71) Applicants: Dot Laboratories, Inc., San Francisco, CA (US); Yale University, New Haven, CT (US)

(72) Inventors: Hugh Taylor, Easton, CT (US); Heather Bowerman, San Francisco, CA (US)

(73) Assignees: Dot Laboratories, Inc., Branford, CT (US); Yale University, New Haven, CT (US)

( * ) Notice: Subject to any disclaimer, the term of this patent is extended or adjusted under 35 U.S.C. 154(b) by 0 days.

(21) Appl. No.: 16/860,792

(22) Filed: Apr. 28, 2020

(65) Prior Publication Data

US 2020/0321077 A1  Oct. 8, 2020

Related U.S. Application Data

(63) Continuation-in-part of application No. PCT/US2019/059006, filed on Oct. 31, 2019.

(60) Provisional application No. 62/840,300, filed on Apr. 29, 2019, provisional application No. 62/753,265, filed on Oct. 31, 2018.

(51) Int. Cl.
| | |
|---|---|
| *G16B 40/10* | (2019.01) |
| *G16B 40/00* | (2019.01) |
| *C12Q 1/686* | (2018.01) |
| *C12Q 1/6874* | (2018.01) |
| *C12Q 1/6883* | (2018.01) |

(52) U.S. Cl.
CPC .............. *G16B 40/10* (2019.02); *C12Q 1/686* (2013.01); *C12Q 1/6874* (2013.01); *C12Q 1/6883* (2013.01); *G16B 40/00* (2019.02); *C12Q 2561/113* (2013.01); *C12Q 2600/112* (2013.01); *C12Q 2600/118* (2013.01); *C12Q 2600/158* (2013.01); *C12Q 2600/178* (2013.01); *G01N 2800/364* (2013.01)

(58) Field of Classification Search
None
See application file for complete search history.

(56) References Cited

U.S. PATENT DOCUMENTS

| | | | |
|---|---|---|---|
| 10,982,282 B2 | 4/2021 | Taylor | |
| 2008/0241113 A1 | 10/2008 | Walton et al. | |
| 2009/0317820 A1 | 12/2009 | Wong et al. | |
| 2012/0093936 A1 | 4/2012 | Lindenberg et al. | |
| 2014/0024590 A1 | 1/2014 | Weidhaas et al. | |
| 2015/0267257 A1 | 9/2015 | Nagarkatti et al. | |
| 2016/0251718 A1 | 9/2016 | Giudice et al. | |
| 2017/0016067 A1* | 1/2017 | Cotter | C12Q 1/6886 |
| 2017/0175190 A1 | 6/2017 | Taylor et al. | |
| 2018/0127828 A1 | 5/2018 | Belli et al. | |
| 2019/0276893 A1 | 9/2019 | Taylor | |
| 2020/0206303 A1 | 7/2020 | Bowerman et al. | |
| 2021/0180134 A1 | 6/2021 | Taylor | |

FOREIGN PATENT DOCUMENTS

| | | |
|---|---|---|
| EP | 2924126 B1 | 4/2018 |
| WO | WO-2010056337 A2 | 5/2010 |
| WO | WO-2012112883 A1 | 8/2012 |
| WO | WO-2013148151 A1 | 10/2013 |
| WO | WO-2015128671 A1 | 9/2015 |
| WO | WO-2015148919 A2 | 10/2015 |
| WO | WO-2018044979 A1 | 3/2018 |
| WO | WO-2019046494 A1 | 3/2019 |
| WO | WO-2020092672 A2 | 5/2020 |

OTHER PUBLICATIONS

Teague et al. (Molecular Endocrinology 23: 265-275, 2009). (Year: 2009).*
Arroyo et al., 2011, "Argonaute2 complexes carry a population of circulating microRNAs independent of vesicles in human plasma." Proc Natl Acad Sci U S A, 108:5003-5008.
Braza-Bols, et al."MicroRNA expression profile in endometriosis: its relation to angiogenesis and fibrinolytic factors", Human Reproduction, GB, (Mar. 6, 2014), vol. 29, No. 5, doi:10.1093/humrep/deu019, ISSN 0268-1161, pp. 978-988, XP055402965.
Chen et al., 2008, "Characterization of microRNAs in serum: a novel class of biomarkers for diagnosis of cancer and other diseases." Cell Res, 18:997-1006.
Chen et al. MiR-125b regulates endometrial receptivity by targeting MMP26 in women undergoing IVF-ET with elevated progesterone on HCG priming day. Scientific reports 6 (2016): 25302.
Cho et al. Aromatase inhibitor regulates let-7 expression and let-7f-induced cell migration in endometrial cells from women with endometriosis. Fertility and sterility 106.3 (2016): 673-680.
Cho, et al. "Circulating microRNAs as potential biomarkers for endometriosis", Fertility and Sterility, (Mar. 13, 2015), vol. 103, No. 5, doi:10.1016/J.FERTNSTERT.2015.02.013, ISSN 0015-0282, p. 1252, XP029155696.
Cosar, et al. Serum microRNAs as diagnostic markers of endometriosis: a comprehensive array-based analysis. Fertil Steril. Aug. 2016;106(2):402-9. doi: 10.1016/j.fertnstert.2016.04.013. Epub May 11, 2016.
D'Hooghe, et al. Lack of an Association between a Polymorphism in the KRAS 3' Untranslated Region (rs61764370) and Endometriosis in a Large European Case-Control Study.Gynecologic and obstetric investigation 84.6 (2019): 575-582.

(Continued)

*Primary Examiner* — Pablo S Whaley
(74) *Attorney, Agent, or Firm* — Wilson Sonsini Goodrich & Rosa

(57) ABSTRACT

Described herein are improved methods for the detection of endometriosis. Generally, the methods include, but are not limited to, applying machine learning algorithm to miRNA levels in order to detect, predict, diagnose, or monitor the presence or absence of endometriosis.

30 Claims, 7 Drawing Sheets
Specification includes a Sequence Listing.

(56) References Cited

OTHER PUBLICATIONS

EP17847431.8 The Partial Supplemental European Search Report dated Apr. 8, 2020.
Gallo et al., 2012, "The majority of microRNAs detectable in serum and saliva is concentrated in exosomes." PLoS One, 7: e30679 (5 pages).
Graham et al. The expression of microRNA-451 in human endometriotic lesions is inversely related to that of macrophage migration inhibitory factor (MIF) and regulates MIF expression and modulation of epithelial cell survival. Human Reproduction 30.3 (2015): 642-652.
Grechukhina, et al. "A polymorphism in a let-7 microRNA binding site of KRAS in women with endometriosis", EMBO Molecular Medicine, (Feb. 3, 2012), vol. 4, No. 3, doi:10.1002/emmm.201100200, ISSN 1757-4676, pp. 206-217, XP055026349.
Joshi et al. Altered expression of microRNA-451 in eutopic endometrium of baboons (*Papio anubis*) with endometriosis. Human Reproduction 30.12 (2015): 2881-2891.
Luong, et al. No evidence for genetic association with the let-7 microRNA-binding site or other common KRAS variants in risk of endometriosis.Human reproduction 27.12 (2012): 3616-3621.
Marsh, et al. "Differential expression of microRNA species in human uterine leiomyonna versus normal myometrium.." Fertil Steril, 89: 1771-1776, Dec. 15, 2008.
May, et al. "Peripheral biomarkers of endometriosis: a systematic review." Hum Reprod Update, 16: 651-674, May 12, 2010.
Mitchell, et al. "Circulating microRNAs as stable blood-based markers for cancer detection." Proc Natl Acad Sci USA, 105: 10513-10518, May 12, 2008.
Moustafa, et al. Accurate diagnosis of endometriosis using serum microRNAs. Am J Obstet Gynecol. Mar. 9, 2020. pii: S0002-9378(20)30321-5. doi: 10.1016/j.ajog.2020.02.050. [Epub ahead of print].
Mu, et al. Expression, regulation and function of MicroRNAs in endometriosis.Die Pharmazie—An International Journal of Pharmaceutical Sciences 71.8 (2016): 434-438.
Naqvi et al., 2016, "Endometriosis Located Proximal to or Remote From the Uterus Differentially Affects Uterine Gene Expression." Reprod Sci, 23:186-191.
Nematian et al. Systemic inflammation induced by microRNAs: endometriosis-derived alterations in circulating microRNA 125b-5p and Let-7b-5p regulate macrophage cytokine production. The Journal of Clinical Endocrinology & Metabolism 103.1 (2017): 64-74.
Nisenblat, et al. Blood biomarkers for the non-invasive diagnosis of endometriosis. Cochrane Database Syst Rev. May 1, 2016;(5):CD012179.
Pan, et al. "The expression profile of micro-RNA in endometrium and endometriosis and the influence of ovarian steroids on their expression." Mol Hum Reprod, 13: 797-806 (Retracted), Aug. 31, 2007.
PCT/US2017/049284 International Search Report and Written Opinion dated Nov. 28, 2017.
PCT/US2018/048649 International Search Report dated Jan. 2, 2019.
PCT/US2020/030284 International Search Report dated Jul. 20, 2020.
Petracco, et al. "MicroRNA 135 Regulates HOXA10 Expression in Endometriosis", Journal of Clinical Endocrinology & Metabolism, (Dec. 1, 2011), vol. 96, No. 12, doi:10.1210/jc.2011-1231, ISSN 0021-972X, pp. E1925-E1933, XP055187310.
Ramon, et al. "microRNAs expression in endometriosis and their relation to angiogenic factors." Hum Reprod, 26: 1082-1090, Jan. 17, 2011.
Rekker, et al. 2013, "Circulating microRNA Profile throughout the menstrual cycle." PLoS One, 8: e81166, (6 pages).
Revised American society for reproductive medicine classification of endometriosis: 1996. Fertility and Sterility. 67: 1997; 817-21.
Sredni et al., 2011, "A Parallel Study of mRNA and microRNA Profiling of Peripheral Blood in Young Adult Women." Front Genet, 2:49 (6 pages).

Suryawanshi, et al. "Plasma microRNAs as novel biomarkers for endometriosis and endometriosis-associated ovarian cancer." Clin Cancer Res, 19: 1213-1224, Jan. 29, 2013.
Taylor, et al. Treatment of Endometriosis-Associated Pain with Elagolix, an Oral GnRH Antagonist.. N Engl J Med. Jul. 6, 2017;377(1):28-40.
Teague, et al. 2010, The role of microRNAs in endometriosis and associated reproductive conditions. Hum Reprod Update, 16: 142-165.
Teague, et al. "MicroRNA-regulated pathways associated with endometriosis." Mol Endocrinol, 23: 265-275, Dec. 2008.
Touw, et al. Data mining in the Life Sciences with Random Forest: a walk in the park or lost in the jungle? Briefings in Bioinformatics 2013, 14 (3): 315-326.
Turchinovich et al., 2011, "Characterization of extracellular circulating microRNA." Nucleic Acids Res, 39:7223-7233.
U.S. Appl. No. 16/329,436 Office Action dated Apr. 8, 2020.
U.S. Appl. No. 15/129,663 Office Action dated Jan. 15, 2020.
Vodolazkaia, et al. "Evaluation of a panel of 28 biomarkers for the non-invasive diagnosis of endometriosis." Hum Reprod, 27: 2698-2711, Jun. 26, 2012.
Wang, et al. "Circulating MicroRNAs Identified in a Genome-Wde Serum MicroRNA Expression Analysis as Noninvasive Biomarkers for Endometriosis", Journal of Clinical Endocrinology & Metabolism, (Jan. 1, 2013), vol. 98, No. 1, doi:10.1210/jc.2012-2415, ISSN 0021-972X, pp. 281-289, XP055127854.
Wang, et al. Analysis of Serum microRNA Profile by Solexa Sequencing in Women With Endometriosis. Reprod Sci. Oct. 2016;23(10):1359-70. doi: 10.1177/1933719116641761. Epub Jul. 13, 2016.
Weber, et al. The microRNA spectrum in 12 body fluids. Clinical chemistry 56.11 (2010): 1733-1741.
Yang, et al. "MicroRNA microarray identifies Let-7i as a novel biomarker and therapeutic target in human epithelial ovarian cancer." Cancer Res, 68: 10307-10314.
Yu, et al. "[Study on microRNA expression in endometrium of luteal phase and its relationship with infertility of endometriosis]", Chung-Hua Fu Ch'an K'o Tsa Chih—Chinese Journal of Obstetricsand Gyneco, Chinese Medical Journals Publ. House, CN, (Dec. 1, 2013), vol. 48, No. 12, ISSN 0529-567X, pp. 907-910, XP008170439.
International search report with written opinion dated Apr. 23, 2020 for PCT/US2019/059006.
Afshar, et al. Changes in eutopic endometrial gene expression during the progression of experimental endometriosis in the baboon, *Papio anubis*. Biology of reproduction 88.2 (2013): 44-1.
Ballard et al., What's the delay? A qualitative study of women's experiences of reaching a diagnosis of endometriosis. Fertility and Sterility, vol. 86, No. 5, Nov. 2006.
Carr, et al. Elagolix, an Oral GnRH Antagonist, Versus Subcutaneous Depot Medroxyprogesterone Acetate for the Treatment of Endometriosis Effects on Bone Mineral Density. Reprod Sci. Nov. 2014; 21(11): 1341-1351.doi: 10.1177/1933719114549848.
Chen et al., Real-time quantification of microRNAs by stem-loop RT-PCR, Nucleic Acids Res., Nov. 27, 2005;33(20):e179.
Cheng, et al. Print CG, Charnock-Jones DS. Activation of mutated K-ras in donor endometrial epithelium and stroma promotes lesion growth in an intact immunocompetent murine model of endometriosis. J Pathol 224.2 (2011): 261-269.
Co-pending U.S. Appl. No. 17/289,882, inventor Taylor; Hugh, filed Apr. 29, 2021.
EP18852025.8 Extended Search Report dated Aug. 3, 2021.
Laudanski, et al. Expression of selected tumor suppressor and oncogenes in endometrium of women with endometriosis. Human reproduction 24.8 (2009): 1880-1890.
Mestdagh et al., High-throughput stem-loop RT-qPCR miRNA expression profiling using minute amounts of input RNA, NucleicAcids Research, 2008, vol. 36, No. 21 e143 (Published online Oct. 21, 2008).
Notice of Allowability dated Feb. 1, 2021 for U.S. Appl. No. 16/329,436 (pp. 1-3).
Ohlsson et al., 2009, "MicroRNA-regulated pathways associated with endometriosis." Mol Endocrinol, 23:265-275.
U.S. Appl. No. 17/184,984 Office Action dated Aug. 4, 2021.

(56) References Cited

OTHER PUBLICATIONS

U.S. Appl. No. 15/129,663 Examiner Interview Summary dated Nov. 20, 2020.
Varkonyi-Gasic et al. Quantitative Stem-Loop RT-PCR for Detection of MicroRNAs. In: Kodama H., Komamine A. (eds) RNAi and Plant Gene Function Analysis. Methods in Molecular Biology (Methods and Protocols), vol. 744. Humana Press, first online Apr. 15, 2011.
Verma, et al. Successful Treatment of Refractory Endometriosis-Related Chronic Pelvic Pain With Aromatase Inhibitors in Premenopausal Patients. Eur J Obstet Gynecol Reprod Biol. Apr. 2009; 143(2):112-5. doi: 10.1016/j.ejogrb.2008.12.002. Epub Feb. 23, 2009.
EP18852025.8 Extended European Search Report dated Aug. 3, 2021.
EP18852025.8 Partial European Search Report dated May 3, 2021.
PCT/US2015/022986 International Preliminary Reporton Patentability dated Sep. 27, 2016.
U.S. Appl. No. 17/184,894 Notice of Allowance dated Sep. 21, 2021.

* cited by examiner

METHOD OF DETECTING AND TREATING ENDOMETRIOSIS IN A FEMALE SUBJECT

CROSS-REFERENCE

This application claims the benefit of U.S. Provisional Application No. 62/840,300, filed Apr. 29, 2019; and this application is a continuation-in-part of PCT/US2019/059006, filed on Oct. 31, 2019; which claims the benefit of U.S. Provisional Application 62/753,265, filed Oct. 31, 2018; all of which are incorporated herein by reference in their entireties.

This application is related to co-pending PCT Application No. PCT/US2020/030284, filed Apr. 28, 2020; which is incorporated herein by reference.

SEQUENCE LISTING

The instant application contains a Sequence Listing which has been submitted electronically in ASCII format and is hereby incorporated by reference in its entirety. Said ASCII copy, created on May 21, 2020, is named 50453-707_501_SL.txt and is 2,953 bytes in size.

BACKGROUND

Endometriosis is a common condition affecting women of pubescent and reproductive age. The disease is thought to be caused by endometrial tissue which migrates from its normal position lining the uterus to other parts of the body, primarily within the abdominal cavity. The ovaries and gut wall are commonly affected. The displaced endometrial tissue, like that in its normal position, grows and declines according to the menstrual cycle as a result of the actions of the ovarian hormones. Endometriosis may cause many symptoms including, but not limited to, abdominal pain, gastrointestinal upset, excessive bleeding, infertility and menstrual disturbance.

Women experiencing recurrent pelvic pain or infertility may be suspected to have endometriosis. Endometriosis, an inflammatory disorder in which endometrial cells proliferate outside the uterus, affects nearly 10% of reproductive age women. It is seen in 50-60% of reproductive aged women with chronic pelvic pain and in up to 50% of women with infertility. Despite its prevalence, endometriosis often goes undiagnosed for years. The average time from the onset of symptoms to a correct diagnosis can range from 5-10 years. The disease can be difficult to recognize based on patients' descriptions of symptoms, especially at early stages, and the definitive diagnosis of the condition presently requires laparoscopic examination, a surgical procedure. Laparoscopy is the current "gold standard" approach for visual confirmation of endometriosis pathology and collection of lesion tissue for histological analysis.

SUMMARY

This disclosure addresses, among other things, a need in the art for minimally-invasive, accurate and more efficient methods of detecting, diagnosing, and monitoring endometriosis.

In one aspect, a method of detecting presence or absence of endometriosis in a female subject is provided, comprising: (a) detecting in a bodily fluid sample from the female subject an expression profile of a panel of miRNAs associated with endometriosis, wherein the panel of miRNAs associated with endometriosis comprises miR-342 or miR451a; (b) applying a machine learning algorithm to the expression profile of the panel of miRNAs associated with endometriosis, wherein the machine learning algorithm has importance measures assigned to miRNA features, and wherein: i. an importance measure is assigned to miR-342 and the importance measure assigned to miR-342 is greater than the importance measure assigned to at least one miRNA selected from the group consisting of: miR-150, miR-3613, miR-451a, let-7b, and miR-125b; or ii. an importance measure is assigned to miR-451a and the importance measure assigned to miR-451a is greater than the importance measure assigned to at least one miRNA selected from the group consisting of: miR-3613, miR-125b, and let-7b; and (c) using the machine learning algorithm to detect presence or absence of endometriosis in the female subject. In some cases, the female subject has symptoms of endometriosis. In some cases, the female subject has symptoms of endometriosis selected from the group consisting of: abdominal pain, gastrointestinal upset, excessive bleeding, infertility and menstrual disturbance. In some cases, the subject has not been previously diagnosed with endometriosis. In some cases, the subject has been previously diagnosed with endometriosis and the method confirms presence of endometriosis in the female subject. In some cases, the method further comprises diagnosing endometriosis in the female subject when the presence of endometriosis is detected. In some cases, the method further comprises prognosing or monitoring endometriosis in the female subject when the presence of endometriosis is detected. In some cases, the method further comprises administering a treatment for endometriosis to the female subject when the presence of endometriosis is detected. In some cases, the method further comprises determining that the female subject has a condition that is not endometriosis when the absence of endometriosis is detected. In some cases, the method further comprises administering a treatment for a non-endometriosis condition to the female subject when the absence of endometriosis is detected. In some cases, the importance measure assigned to miR-342 is greater than the importance measure assigned to at least one miRNA selected from the group consisting of: miR-150, miR-3613, miR-451a, let-7b, and miR-125b. In some cases, the importance measure assigned to miR-342 is less than the importance measure assigned to at least one other miRNA. In some cases, the importance measure assigned to miR-342 is greater than the importance measure assigned to at least one miRNA selected from the group consisting of: miR-150, miR-3613, miR-451a, let-7b, and miR-125b; and is less than the importance measure assigned to at least one miRNA selected from the group consisting of: miR-150, miR-3613, miR-451a, let-7b, and miR-125b. In some cases, the importance measure assigned to miR-342 is less than the importance measure assigned to at least two other miRNA. In some cases, the importance measure assigned to miR-342 is greater than the importance measure assigned to at least two miRNA selected from the group consisting of: miR-150, miR-3613, miR-451a, let-7b, or miR-125b. In some cases, the importance measure assigned to miR-342 is greater than the importance measure assigned to at least three miRNA selected from the group consisting of: miR-150, miR-3613, miR-451a, let-7b, or miR-125b. In some cases, the importance measure assigned to miR-342 is greater than the importance measure assigned to at least four miRNA selected from the group consisting of: miR-150, miR-3613, miR-451a, let-7b, and miR-125b. In some cases, the importance measure assigned to miR-342 is greater than the importance measure assigned to miR-150, miR-3613, miR-451a, let-7b, and miR-125b. In some cases, the importance measure assigned to miR-451 a is greater than the importance measure assigned to at least one miRNA selected from the group consisting of: miR-3613, miR-125b and let-7b. In some cases, the importance measure assigned to miR-451a is greater than the importance measure assigned to at least two miRNA selected from the group consisting of: miR-3613, miR-125b and let-7b. In some cases, the importance measure assigned to miR-451a is greater than the importance measure assigned to miR-3613, miR-125b and let-7b. In some cases, the importance measures are assigned such that the ranking of the importance measures from highest to lowest is: miR-342, miR-451a, miR-3613, miR-125b, let-7b, and miR-150. In some cases, the bodily fluid sample comprises cells. In some cases, the bodily fluid sample is a cell-free sample. In some cases, the bodily fluid sample is a blood sample, a plasma sample, a saliva sample, or a serum sample. In some cases, the panel of miRNA are cell-free miRNA. In some cases, the panel of miRNA are cell-associated miRNA or exosome-associated miRNA. In some cases, the applying a machine learning algorithm to the expression profile comprises applying a machine learning algorithm with specific importance measure rankings assigned to the miRNA features, wherein the ranking from highest to lowest is miR-342, miR-451a, miR-3613, miR-125b, let-7b, and miR-150. In some cases, the machine learning algorithm is a random forest algorithm, k-nearest-neighbors algorithm (KNN), support vector machine (SVM), or Naive Bayes. In some cases, the machine learning algorithm is a random forest algorithm. In some cases, the method detects endometriosis in a population of women with a specificity of greater than 80%. In some cases, the population of women is premenopausal women. In some cases, the population of women comprises women with leiomyomas, cystadenomas, chronic pelvic infections, teratomas, endometriomas, or paratubal cysts. In some cases, the population of women comprises women with Stage I/II endometriosis. In some cases, the population of women comprises women with Stage III/IV endometriosis or women with all four stages of endometriosis (Stage I/II/III/IV). In some cases, the population of women comprises women having received hormone therapy within 3 months of the date on which the sample was obtained or women at any phase of their menstrual cycle. In some cases, the population of women comprises a cohort comprising at least 100 women. In some cases, the population of women comprises a cohort comprising at least 1000 women. In some cases, the machine learning algorithm is trained on expression data from at least 100 samples. In some cases, the machine learning algorithm is trained on expression data from at least 500 samples. In some cases, the machine learning algorithm is trained on expression data from at least 1000 samples. In some cases, the machine learning algorithm is trained on a population of women comprising women having stages I-IV endometriosis. In some cases, the method has an AUC for detecting endometriosis of greater than 0.85 in a population of women. In some cases, the method has an AUC for detecting endometriosis of greater than 0.90 in a population of women. In some cases, the method has an AUC for detecting endometriosis of greater than 0.92 in a population of women. In some cases, the method detects endometriosis in a population of women with a specificity of greater than 80%. In some cases, the method detects endometriosis in a population of women with a specificity of greater than 85%. In some cases, the method detects endometriosis in a population of women with a specificity of greater than 90%. In some cases, the method detects endometriosis in a population of women with a specificity of greater than 92%. In some cases, the method detects endometriosis in a population of women with a specificity of greater than 95%. In some cases, the method detects endometriosis in a population of women with a sensitivity of greater than 80%. In some cases, the method detects endometriosis in a population of women with a sensitivity of greater than 85%. In some cases, the method detects endometriosis in a population of women with a sensitivity of greater than 90%. In some cases, the method detects endometriosis in a population of women with a specificity of greater than 90% and a sensitivity of less than 85%. In some cases, the method detects endometriosis in a population of women with a specificity of greater than 95% and a sensitivity of less than 85%. In some cases, the method detects endometriosis in a population of women with a sensitivity of less than 90%. In some cases, the method detects endometriosis in a population of women with a sensitivity of less than 85%. In some cases, the method detects endometriosis in a population of women with a sensitivity of less than 80%. In some cases, the method further comprises treating the female subject with a treatment that does not involve surgery when the absence of endometriosis is detected. In some cases, the method further comprises administering a treatment to the female subject when the presence of endometriosis is detected, wherein the treatment comprises a hormonal treatment, surgery, laparoscopic surgery, a statin, a non-steroidal anti-inflammatory drug (NSAID), an oral contraceptive, a progestin, a gonadotrophin releasing (GnRH) agonist, a GnRH antagonist, an androgen, an antiprogesterone, a selective estrogen receptor modulator (SERM), a selective progesterone receptor modulator (SPRM), atorvastatin, cerivastatin, fluvastatin, lovastatin, mevastatin, pitavastatin, pravastatin, rosuvastatin, simvastatin, paracetamol, a COX-2 inhibitor, or aspirin. In some cases, the miRNA expression level is detected by quantitative real-time polymerase chain reaction (RT-PCR), microarray, sequencing, or Next Generation sequencing.

In another aspect, a method of classifying endometriosis in a female subject is provided comprising: (a) obtaining a bodily fluid sample comprising miRNA wherein the bodily fluid sample is from a female subject; (b) performing quantitative real-time polymerase chain reaction, microarray assay or sequencing assay on a set of miRNA within the bodily fluid sample, wherein the set of miRNA comprises two or more different miRNA associated with endometriosis; (c) comparing to an amount of a control RNA, an amount of the two or more different miRNA associated with endometriosis in the biological sample to determine a normalized miRNA level for the two or more different miRNAs in the bodily fluid sample; (d) classifying the female subject as positive or negative for endometriosis by inputting the normalized miRNA levels to a trained algorithm, wherein the trained algorithm has importance rankings of the two or more different miRNA and wherein the trained algorithm is optimized for a specificity that is higher than sensitivity by selecting an optimal cutoff point on a receiver operating characteristic (ROC) curve or on a voting percentage distribution for the two or more different miRNA associated with endometriosis; and (e) outputting a report on a computer screen that identifies the female subject as either positive or negative for endometriosis based on the classifying of the female subject as positive or negative for endometriosis in (d). In some cases, the trained algorithm is optimized to detect endometriosis with a specificity of greater than 80% in a population of women. In some cases, the trained algorithm is optimized to detect endometriosis with a specificity of greater than 90% and a sensitivity less than 85% in a population of women. In some cases, the trained algorithm detects Stage I/II endometriosis with a specificity of greater than 90%, or greater than 95% in a population of women. In some cases, the method has an AUC for detecting endometriosis of greater than 0.85 in a population of women. In some cases, the method has an AUC for detecting endometriosis of greater than 0.9 in a population of women. In some cases, the method has an AUC for detecting endometriosis of greater than 0.92 in a population of women. In some cases, the method detects endometriosis in a population of women with a specificity of greater than 85%. In some cases, the method detects endometriosis in a population of women with a specificity of greater than 90%. In some cases, the method detects endometriosis in a population of women with a specificity of greater than 95%. In some cases, the method detects endometriosis in a population of women with a sensitivity of greater than 80%. In some cases, the method detects endometriosis in a population of women with a sensitivity of greater than 90%. In some cases, the method detects endometriosis in a population of women with a sensitivity of less than 90%, less than 85%, or less than 80%. In some cases, the population of women comprises at least 100 women. In some cases, the population of at least 100 women comprises women with leiomyomas. In some cases, the method has an area under curve (AUC) value greater than 0.85 irrespective of endometriosis stage or hormonal treatment. In some cases, the method further comprises administering a treatment for endometriosis to the female subject after the report identifies the female subject as being negative for endometriosis. In some cases, the method further comprises administering a treatment for a non-endometriosis condition to the female subject after the report identifies the female subject as being negative for endometriosis. In some cases, the method further comprises repeating (a)-(e) on an additional bodily fluid sample obtained at least three months after the report identifies the female subject as being negative for endometriosis. In some cases, the trained algorithm assigns an importance measure to miR-342 that is greater than the importance measure assigned to at least one miRNA selected from the group consisting of: miR-150, miR-3613, miR-451a, let-7b, and miR-125b. In some cases, the importance measure assigned to miR-342 is less than the importance measure assigned to at least one other miRNA. In some cases, the importance measure assigned to miR-342 is greater than the importance measure assigned to at least two miRNA selected from the group consisting of: miR-150, miR-3613, miR-451a, let-7b, or miR-125b. In some cases, the importance measure assigned to miR-342 is greater than the importance measure assigned to at least three miRNA selected from the group consisting of: miR-150, miR-3613, miR-451a, let-7b, or miR-125b. In some cases, the importance measure assigned to miR-342 is greater than the importance measure assigned to at least four miRNA selected from the group consisting of: miR-150, miR-3613, miR-451a, let-7b, and miR-125b. In some cases, the importance measure assigned to miR-342 is greater than the importance measure assigned to miR-150, miR-3613, miR-451a, let-7b, and miR-125b. In some cases, the importance measure assigned to miR-451a is greater than the importance measure assigned to at least one miRNA selected from the group consisting of: miR-3613, miR-125b and let-7b. In some cases, the importance measure assigned to miR-451a is greater than the importance measure assigned to at least two miRNA selected from the group consisting of: miR-3613, miR-125b and let-7b. In some cases, the importance measure assigned to miR-451a is greater than the importance measure assigned to miR-3613, miR-125b and let-7b. In some cases, the importance measures are assigned such that the ranking of the importance measures from highest to lowest is: miR-342, miR-451a, miR-3613, miR-125b, let-7b, and miR-150. In some cases, the bodily fluid sample comprises cells. In some cases, the bodily fluid sample is a cell-free sample. In some cases, the bodily fluid sample is a blood sample, a plasma sample, a saliva sample, or a serum sample. In some cases, the applying a machine learning algorithm to the expression profile comprises applying a machine learning algorithm with specific importance measure rankings assigned to the miRNA features, wherein the ranking from highest to lowest is miR-342, miR-451a, miR-3613, miR-125b, let-7b, and miR-150. In some cases, the machine learning algorithm is a random forest algorithm, k-nearest-neighbors algorithm (KNN), support vector machine (SVM), or Naive Bayes. In some cases, the machine learning algorithm is a random forest algorithm. In some cases, the population of women is premenopausal women. In some cases, the population of women comprises women with leiomyomas, cystadenomas, chronic pelvic infections, teratomas, endometriomas, or paratubal cysts, in any combination. In some cases, the population of women comprises women with Stage I/II endometriosis. In some cases, the population of women comprises women with Stage III/IV endometriosis or women with all four stages of endometriosis (Stage I/II/III/IV). In some cases, the population of women comprises women having received hormone therapy within 3 months of the date on which the sample was obtained or women at any phase of their menstrual cycle. In some cases, the population of women comprises a cohort comprising at least 100 women. In some cases, the population of women comprises a cohort comprising at least 500 women. In some cases, the population of women comprises a cohort comprising at least 1000 women. In some cases, the machine learning algorithm is trained on expression data from at least 100 samples. In some cases, the machine learning algorithm is trained on expression data from at least 1000 samples. In some cases, the machine learning algorithm is trained on a population of women comprising women having stages I-IV endometriosis. In some cases, the method further comprises treating the female subject with a treatment that does not involve surgery when the absence of endometriosis is detected. In some cases, the method further comprises administering a treatment to the female subject when the presence of endometriosis is detected, wherein the treatment comprises a hormonal treatment, surgery, laparoscopic surgery, a statin, a non-steroidal anti-inflammatory drug (NSAID), an oral contraceptive, a progestin, a gonadotrophin releasing (GnRH) agonist, a GnRH antagonist, an androgen, an antiprogesterone, a selective estrogen receptor modulator (SERM), a selective progesterone receptor modulator (SPRM), atorvastatin, cerivastatin, fluvastatin, lovastatin, mevastatin, pitavastatin, pravastatin, rosuvastatin, simvastatin, paracetamol, a COX-2 inhibitor, or aspirin.

In yet another aspect, a method of diagnosing and treating endometriosis in a female subject is provided, comprising: (a) detecting in a saliva sample from the female subject an expression profile of a panel of miRNAs associated with endometriosis, wherein the panel of miRNAs associated with endometriosis comprises miR-125b and at least one other miRNA; (b) applying a machine learning algorithm to the expression profile of the panel of miRNAs associated with endometriosis, wherein the machine learning algorithm has importance measures assigned to miRNA features, and wherein the importance measure of miR-125b is greater than the importance measure of miR-150, miR-3613, miR-451a, let-7b, or miR-342; (c) using the machine learning algorithm to diagnose endometriosis in the female subject; and (d) treating the endometriosis diagnosed in the female subject with a treatment for endometriosis. In some cases, applying a machine learning algorithm to the expression profile comprises applying a machine learning algorithm with specific importance measures assigned to the miRNA features, wherein the importance measure of miR-125b is greater than at least one of miR-150, let-7b, miR-451a, or miR-3613. In some cases, applying a machine learning algorithm to the expression profile comprises applying a machine learning algorithm with specific importance measures assigned to the miRNA features, wherein the importance measure of miR-125b is greater than at least two of miR-150, let-7b, miR-451 a, or miR-3613. In some cases, applying a machine learning algorithm to the expression profile comprises applying a machine learning algorithm with specific importance measures assigned to the miRNA features, wherein the importance measure of miR-125b is greater than at least three of miR-150, let-7b, miR-451a, or miR-3613. In some cases, applying a machine learning algorithm to the expression profile comprises applying a machine learning algorithm with specific importance measures assigned to the miRNA features, wherein the importance measure of miR-125b is greater than miR-150, let-7b, miR-451a, and miR-3613.

In yet another aspect, a method of characterizing a female subject as having endometriosis is provided comprising: (a) obtaining a bodily fluid sample comprising miRNA wherein the bodily fluid sample is from a female subject; (b) performing quantitative real-time polymerase chain reaction, microarray assay, or sequencing of a set of miRNA within the bodily fluid sample, wherein the set of miRNA comprises two or more different miRNA associated with endometriosis; (c) comparing to an amount in a control RNA, an amount of the two or more different miRNA associated with endometriosis in the biological sample to determine a normalized miRNA level for the two or more different miRNAs in the bodily fluid sample; (d) classifying the female subject as positive or negative for endometriosis by inputting the normalized miRNA levels to a trained algorithm, wherein the trained algorithm is optimized for a sensitivity of at least 80% by selecting an optimal cutoff point on a receiver operating characteristic (ROC) curve for the two or more different miRNA associated with endometriosis and wherein the trained algorithm has importance rankings of the two or more different miRNA; and (e) outputting a report on a computer screen that identifies the female subject as either positive or negative for endometriosis based on the classifying of the female subject as positive or negative for endometriosis in (d).

In yet another aspect, a method of characterizing a female subject as not having endometriosis is provided comprising: (a) obtaining a bodily fluid sample comprising miRNA wherein the bodily fluid sample is from a female subject with abdominal pain, gastrointestinal upset, excessive bleeding, infertility or menstrual disturbance and said subject has not been previously diagnosed with endometriosis; (b) performing quantitative real-time polymerase chain reaction or sequencing of a set of miRNA within the bodily fluid sample, wherein the set of miRNA comprises two or more different miRNA associated with endometriosis; (c) comparing to an amount in a control RNA, an amount of the two or more different miRNA associated with endometriosis in the biological sample to determine a normalized miRNA level for the two or more different miRNAs in the bodily fluid sample; (d) classifying the female subject as positive or negative for endometriosis by inputting the normalized miRNA levels to a trained algorithm, wherein the trained algorithm is optimized for a specificity of at least 80% by selecting an optimal cutoff point on a receiver operating characteristic (ROC) curve for the two or more different miRNA associated with endometriosis and wherein the trained algorithm has importance rankings of the two or more different miRNA; and (e) outputting a report on a computer screen that identifies the female subject as either positive or negative for endometriosis based on the classifying of the female subject as positive or negative for endometriosis in (d). In some cases, the trained algorithm calculates a voting score indicative of likelihood of having endometriosis. In some cases, the trained algorithm classifies the female subject as having endometriosis when the voting score is greater than 36%. In some cases, the method has an area under curve (AUC) value greater than 0.85 for Stage I/II endometriosis. In some cases, the method has an area under curve (AUC) value greater than 0.85 for distinguishing between endometriosis and leiomyomas. In some cases, the method has an area under curve (AUC) value greater than 0.85 irrespective of endometriosis stage or hormonal treatment. In some cases, the method is optimized for a specificity greater than 90% and a sensitivity less than 85%.

In yet another aspect, a method of detecting endometriosis in a female subject is provided, comprising: (a) detecting in a sample comprising miRNA from the subject an expression profile of a panel of miRNAs associated with endometriosis; (b) applying a machine learning algorithm to the expression profile to detect endometriosis in the sample from the subject, wherein the machine learning algorithm is trained on a group of miRNA features selected from the group consisting of: (i) miR-342, miR-451a, and miR-3613; (ii) miR-342, miR-451a, miR-3613, and miR-125b; (iii) miR-342, miR-451a, miR-3613, miR-125b, and let-7b; (iv) miR-342, miR-451a, let-7b, and miR-125b; (v) miR-342, miR-451a, let-7b, and miR-3613; (vi) miR-342, miR-451a, and let-7b; (vii) miR-125b, miR-150, miR-342, miR-451a, and let-7b; and (viii) miR-125b, miR-150, miR-342, miR-3613, miR-451a, and let-7b. In some cases, the method further comprises obtaining the sample comprising miRNA from the subject, prior to (a). In some cases, the sample is a saliva sample. In some cases, the sample is a serum sample. In some cases, the machine learning algorithm is a random forest algorithm, k-nearest-neighbors algorithm (KNN), support vector machine (SVM), or Naive Bayes. In some cases, the method has an AUC for detecting endometriosis of greater than 0.85 in a population of women. In some cases, the population of women is premenopausal women. In some cases, the population of women is premenopausal and over 18. In some cases, the population of women is premenopausal and under 49. In some cases, the population of women is negative for critical anemia, hyperplasia, polyps, and malignancy. In some cases, the population of women includes women having received hormone therapy within 3 months of the date on which the sample was obtained. In some cases, the hormone therapy includes birth control pills or GnRH agonists. In some cases, the machine learning algorithm is trained on expression data of at least 100 samples. In some cases, the machine learning algorithm is trained on a population of women with surgically-confirmed endometriosis. In some cases, the machine learning algorithm is trained on a population of women comprising women having stage I or II endometriosis. In some cases, the machine learning algorithm is trained on a population of women comprising women having stages I-IV endometriosis. In some cases, applying a machine learning algorithm to the expression profile comprises applying a machine learning algorithm with specific importance measures assigned to the miRNA features, wherein the importance measure of miR-342 is greater than at least one of miR-150, let-7b, or miR-125. In some cases, applying a machine learning algorithm to the expression profile comprises applying a machine learning algorithm with specific importance measures assigned to the miRNA features, wherein the importance measure of miR-125b is greater than one of miR-150, let-7b, miR-451a, or miR-3613. In some cases, applying a machine learning algorithm to the expression profile comprises training the machine learning algorithm on the group of miRNA features of (viii) and applying a machine learning algorithm with specific importance measures assigned to the miRNA features, wherein the ranking of the miRNA features from highest to lowest is miR-125b, let-7b, miR-3613, miR-150, miR-342, and miR-451a. In some cases, applying a machine learning algorithm to the expression profile comprises training the machine learning algorithm on the group of miRNA features in (viii) and applying a machine learning algorithm with specific importance measure rankings assigned to the miRNA features, wherein the ranking from highest to lowest is miR-342, miR-451a, miR-3613, miR-125b, let-7b, and miR-150. In some cases, applying a machine learning algorithm to the expression profile comprises training the machine learning algorithm on the group of miRNA features in (viii) and applying an machine algorithm with specific importance measures assigned to the miRNA features, wherein the importance measure ranking of the miRNA features is according to any column in Table 9.

In yet another aspect, a method is provided comprising: (a) storing information related to the condition of a female patient in a standardized format in a plurality of network-based non-transitory storage devices; (b) providing remote access to users over a network so that at least one user can update the information related to the condition of a female patient in real time through a graphical user interface, wherein the at least one user provides the updated information in the form of an expression profile of miRNAs from the female patient; (c) converting, by a content server, the expression profile of the miRNAs from the female patient to a likelihood of the female patient having endometriosis using the application of a machine learning algorithm; (d) storing the likelihood of the female patient having endometriosis; (e) automatically generating a message containing the likelihood of the female patient having endometriosis by the content server whenever the updated information has been stored; and (f) transmitting the message to all of the users over the computer network in real time, so that each user has immediate access to the likelihood of the female patient having endometriosis. In some cases, the machine learning algorithm is trained on a group of miRNA features selected from the group consisting of: (i) miR-342, miR-451a, and miR-3613; (ii) miR-342, miR-451a, miR-3613, and miR-125b; (iii) miR-342, miR-451a, miR-3613, miR-125b, and let-7b; (iv) miR-342, miR-451a, let-7b, and miR-125b; (v) miR-342, miR-451a, let-7b, and miR-3613; (vi) miR-342, miR-451a, and let-7b; (vii) miR-125b, miR-150, miR-342, miR-451a, and let-7b; and (viii) miR-125b, miR-150, miR-342, miR-3613, miR-451a, and let-7b. In some cases, the method further comprises obtaining a sample comprising miRNA from the subject. In some cases, the sample is a blood sample, plasma sample, or serum sample. In some cases, the sample is a saliva sample. In some cases, the sample is a serum sample. In some cases, the machine learning algorithm is a random forest algorithm, k-nearest-neighbors algorithm (KNN), support vector machine (SVM), or Naive Bayes. In some cases, the method has an AUC for detecting endometriosis of greater than 0.85 in a population of women. In some cases, the population of women includes women having received hormone therapy within 3 months of the date on which the sample was obtained. In some cases, the hormone therapy includes birth control pills or GnRH agonists. In some cases, the sample is a cell-free serum sample. In some cases, the sample is a cell-free saliva sample. In some cases, the method further comprises administering a treatment to the subject to treat the endometriosis based on the likelihood reported in (e). In some cases, the treatment comprises a hormonal treatment, a statin, or a non-steroidal anti-inflammatory drug (NSAID). In some cases, the hormonal treatment comprises an oral contraceptive, a progestin, a GnRH agonist, a GnRH antagonist, an androgen, an antiprogesterone, a SERM, or SPRM. In some cases, the statin comprises atorvastatin, cerivastatin, fluvastatin, lovastatin, mevastatin, pitavastatin, pravastatin, rosuvastatin, or simvastatin. In some cases, the NSAID comprises paracetamol, a COX-2 inhibitor, or aspirin.

In some aspects, the present disclosure provides for a method of detecting endometriosis in a female subject, comprising: (a) detecting in a sample from the subject an expression profile of a panel of miRNAs associated with endometriosis; (b) applying a machine learning algorithm to the expression profile to detect endometriosis in the sample from the subject, wherein the machine learning algorithm is trained on a group of miRNA features selected from the group consisting of: (i) miR-342, miR-451a, and miR-3613; (ii) miR-342, miR-451a, miR-3613, miR-125b; (iii) miR-342, miR-451a, miR-3613, miR-125b, let-7b; (iv) miR-342, miR-451a, let-7b, miR-125b; (v) miR-342, miR-451a, let-7b, miR-3613; (vi) miR-342, miR-451a, let-7b; (vii) miR-125b, miR-150, miR-342, miR-451a, let-7b; and (viii) miR-125b, miR-150, miR-342, miR-3613, miR-451a, and let-7b. In some embodiments, the method comprises obtaining a sample comprising miRNA from the subject. In some embodiments, the sample is a blood sample. In some embodiments, the sample is a serum sample. In some embodiments, the sample is a plasma sample. In some embodiments, the sample is a cell-free or acellular blood, plasma, or serum sample. In some embodiments, the sample is a blood sample collected by venipuncture into a collection tube without additional additives, followed by centrifugation to remove cells. In some embodiments, the blood sample is centrifuged or filtered to remove cells. In some embodiments, the sample is a blood, plasma or serum sample. In some embodiments, the sample is a urine sample. In some embodiments, the sample is a bodily fluid sample. In some embodiments, the bodily fluid is sweat, saliva, tears, urine, blood, plasma, serum, vaginal fluid, cervico-vaginal fluid, whole blood, menstrual effluent, menstrual blood, spinal fluid, pulmonary fluid, or sputum. In some embodiments, the machine learning algorithm is a random forest algorithm, k-nearest-neighbors algorithm (KNN), support vector machine (SVM), or Naive Bayes. In some embodiments, the algorithm is a random forest algorithm. In some embodiments, the method has an AUC for detecting endometriosis of greater than 0.85 in a population of women. In some embodiments, the population of women is premenopausal women. In some embodiments, the population of women is premenopausal and over 18. In some embodiments, the population of women is premenopausal and under 49. In some embodiments, the population of women is negative for critical anemia, hyperplasia, polyps, and malignancy. In some embodiments, the population of women includes women having received hormone therapy within 3 months of the date on which the sample was obtained. In some embodiments, the hormone therapy includes birth control pills and/or GnRH agonists. In some embodiments, the algorithm is trained on expression data from at least 100 samples. In some embodiments, the algorithm is trained on expression data from at least 50 samples. In some embodiments, the algorithm is trained on expression data from at least 200 samples. In some embodiments, the algorithm is trained on expression data from at least 500 samples or at least 1000 sample. In some embodiments, the algorithm is trained on a population of women with surgically-confirmed endometriosis. In some embodiments, the algorithm is trained on a population of women comprising women having stage I or II endometriosis. In some embodiments, the algorithm is trained on a population of women comprising women having stages I-IV endometriosis. In some embodiments, applying a machine learning algorithm (e.g., random forest algorithm) to the expression profile comprises assigning importance measures to the miRNA features, wherein the importance measure of miR-342 is greater than one of miR-150, let-7b, or miR-125. In some embodiments, applying a machine learning algorithm to the expression profile comprises assigning importance measures the miRNA features, wherein the importance measure of miR-125b is greater than one of miR-150, let-7b, or miR-125. In some embodiments, applying a machine learning algorithm to the expression profile comprises training the machine learning algorithm on the features in (viii) and assigning importance measures the miRNA features, wherein the importance measure ranking of the miRNA features from highest to lowest is miR-125b, let-7b, miR-2613, miR-150, miR-342, and miR-451a. In some embodiments, applying a machine learning algorithm to the expression profile comprises training the machine learning algorithm on the features in (viii) and assigning importance measures the miRNA features, wherein the importance measure (e.g., feature importance) ranking of the miRNA features from highest to lowest is miR-342, miR-451a, miR-3613, miR-125b, let-7b, and miR-150. In some embodiments, applying a machine learning algorithm to the expression profile comprises training the machine learning algorithm on the features in (viii) and assigning importance measures the miRNA features, wherein the importance measure ranking of the miRNA features is according to Table 9. In some embodiments, the method further comprises detecting, diagnosing, or assessing risk of endometriosis in the female subject using a supervised learning algorithm having feature importances assigned in Table 9. In some embodiments, the methods further comprises administering an endometriosis treatment to treat the endometriosis detected or diagnosed in the female subject.

In some aspects, the present disclosure provides for a method comprising: (a) storing information related to the condition of a female patient in a standardized format in a plurality of network-based non-transitory storage devices; (b) providing remote access to users over a network so that at least one user can update the information related to the condition of a female patient in real time through a graphical user interface, wherein the at least one user provides the updated information in the form of an expression profile of miRNAs from the female patient; (c) converting, by a content server, the expression profile of the miRNAs from the female patient to a likelihood of the female patient having endometriosis using the application of a machine learning algorithm; (d) storing the likelihood of the female patient having endometriosis; (e) automatically generating a message containing the likelihood of the female patient having endometriosis by the content server whenever the updated information has been stored; and (f) transmitting the message to at least some of the users over the computer network in real time, so that the users have immediate access to the likelihood of the female patient having endometriosis. In some embodiments, the machine learning algorithm is trained on a group of miRNA features selected from the group consisting of: (i) miR-342, miR-451a, and miR-3613; (ii) miR-342, miR-451a, miR-3613, miR-125b; (iii) miR-342, miR-451a, miR-3613, miR-125b, let-7b; (iv) miR-342, miR-451a, let-7b, miR-125b; (v) miR-342, miR-451a, let-7b, miR-3613; (vi) miR-342, miR-451a, let-7b; (vii) miR-125b, miR-150, miR-342, miR-451a, let-7b; and (viii) miR-125b, miR-150, miR-342, miR-3613, miR-451a, and let-7b. In some embodiments, the method comprises obtaining a sample comprising miRNA from the subject. In some embodiments, the sample is a saliva sample. In some embodiments, the sample is a serum sample. In some embodiments, the sample is a blood, plasma or serum sample. In some embodiments, the sample is a urine sample. In some embodiments, the sample is a bodily fluid sample. In some embodiments, the bodily fluid is sweat, saliva, tears, urine, blood, plasma, serum, vaginal fluid, cervico-vaginal fluid, whole blood, menstrual effluent, menstrual blood, spinal fluid, pulmonary fluid, or sputum. In some embodiments, the machine learning algorithm is a random forest algorithm, k-nearest-neighbors algorithm (KNN), support vector machine (SVM), and Naive Bayes. In some embodiments the machine learning algorithm is a random forest algorithm. In some embodiments, the method has an AUC for detecting endometriosis of greater than 0.85 in a population of women. In some embodiments, the population of women includes women having received hormone therapy within 3 months of the date on which the sample was obtained. In some embodiments, the hormone therapy comprises birth control pills or GnRH agonists. In some embodiments, the method further comprises detecting, diagnosing, or assessing risk of endometriosis in the female subject based on the importance measures. In some embodiments, the methods further comprises administering an endometriosis treatment to treat the endometriosis detected or diagnosed in the female subject.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Overview

Figure 1:
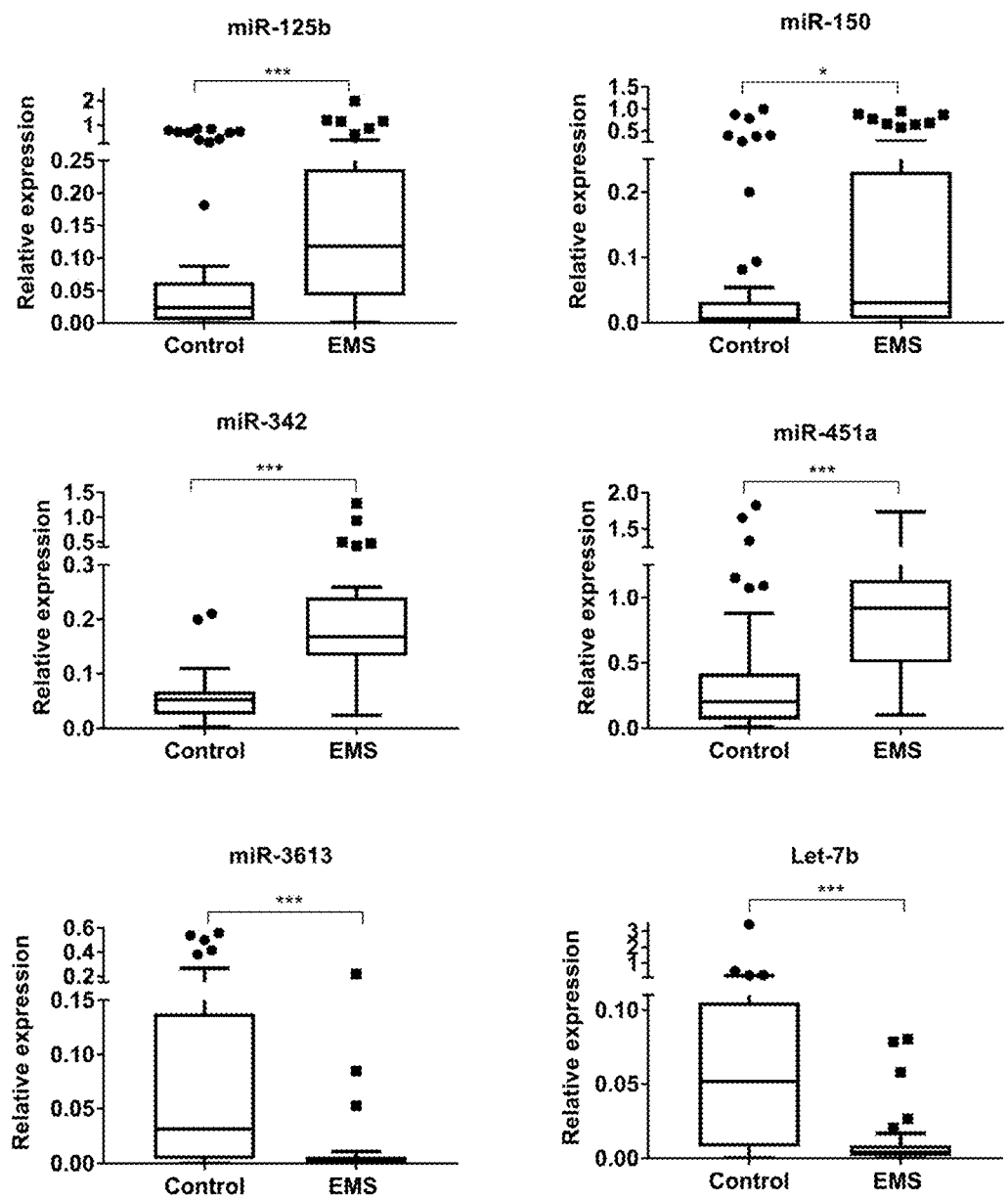
FIG. 1 depicts scatter and box plots of miRNA expression in control vs. endometriosis patient serum demonstrating that all markers are effective for identifying endometriosis to some degree. Data shows expression levels of six miRNAs (miR-125b, miR-451a, miR-3613, miR-150, miR-342, and let-7b), normalized relative to levels of the small nuclear RNA gene U6. Data are plotted with the median indicated by a line and the interquartile range (IQR) marked by the box. Whiskers and outliers are displayed according to the Tukey method, which plots whiskers at the points falling less than or equal to 1.5 times IQR (25th percentile minus IQR or 75th percentile plus IQR), with points falling outside this range plotted individually. *p<0.05, ***p<0.001, using the Mann-Whitney U test followed by the Bonferroni correction for multiple comparisons.

Considering that delayed diagnosis of endometriosis may compound the costs and negative experiences of women, identifying and treating the disease sooner would likely greatly benefit women, potentially preventing complications of advanced disease including infertility, while decreasing the economic burden of untreated endometriosis. Although laparoscopy is the current clinical recommendation for a definitive diagnosis of endometriosis, it carries costs and risk to the patient, and has limitations for accurately identifying endometriosis, especially if performed without histological confirmation. Surgical intervention is rarely undertaken for early disease or in patients with an unclear presentation. Imaging methods such as ultrasound may be appropriate to detect advanced endometriosis or endometriomas, but are insufficient to detect most disease such as common peritoneal lesions or adhesions.

Analyzing a combination of biomarkers, rather than a single biomarker, may improve detection of endometriosis. Serum cancer antigen CA-125 has been utilized as a circulating marker for the disease, however it does not have sufficient diagnostic sensitivity or specificity, since increased CA-125 levels mainly reflect advanced stages of endometriosis, and are also elevated in other diseases (e.g., fibroids, ovarian cancer, pelvic inflammatory disorder). A systematic review of 141 studies of 122 blood biomarkers, including endometrial antibodies, reported that none of the biomarkers studied in the review met the criteria for a triage or replacement diagnostic test (see Nisenblat et al. Cochrane Database Syst Rev. 2016(5):Cd012179).

The present disclosure provides novel methods for characterizing, monitoring, and analyzing samples from subjects having a symptom of endometriosis, having endometriosis, at risk of having endometriosis, or suspected of having endometriosis. This disclosure also provides methods of detecting, diagnosing, monitoring, and/or prognosing such subjects, as well as methods of treating such subjects. Generally, the methods provided herein involve the detection or quantitation of biomarkers in a sample from a subject, particularly non-coding RNA (e.g., miRNA). In some cases, the methods provided herein involve application of a machine learning algorithm.

Definitions

As used herein, the term "cell-free", when used in reference to a nucleic acid, refers to a nucleic acid that was not associated with a cell at the time the nucleic acid was obtained from the body. For example, nucleic acids may be present in a body fluid such as blood or saliva in a cell-free state in that they are not associated with a cell. However, the cell-free nucleic acids may have originally been associated with a cell, such as an endometrial cell prior to entering the bloodstream or other body fluid. In contrast, nucleic acids that are solely associated with cells in the body are generally not considered to be "cell-free." For example, nucleic acids extracted directly from cells are generally not considered "cell-free" as the term is used herein.

As used herein, a "cell-free sample" generally refers to a biological sample, particularly a biological fluid sample, in which cells are absent or are present in such low amounts that the miRNA level determined reflects its level in the liquid portion of the sample, rather than in the cellular portion. In some instances, the cell-free portion of the sample is obtained by centrifugation, filtration, fractionation column, or other method. In some cases, the body fluid may be naturally cell-free. Typically, a cell-free body fluid sample contains no intact cells; however, it may contain cell fragments, exosomes, or cellular debris. In some cases, the sample is processed or used immediately following sample collection; in some cases, the sample is stored for later use. Any suitable storage method known in the art may be used to store the body fluid sample, for example, the sample may be frozen at about −20.degrees C. to about −70.degrees C.

As used herein, a "cell-free serum" sample is generally a serum sample that is processed almost immediately following collection in order to avoid disruption of cells, such as by a clotting mechanism.

Conventional notation is used herein to describe polynucleotide sequences: the left-hand end of a single-stranded polynucleotide sequence is the 5'-end; the leftward direction of a double-stranded polynucleotide sequence is referred to as the 5'-direction.

The terms "subject," "patient," "individual," and the like are used interchangeably herein, and refer to any animal, amenable to the methods described herein. In certain non-limiting embodiments, the patient, subject, or individual is a human. In some cases, the methods provided herein may involve cells from such subject, patient or individual. In some cases, the method may be conducted, at least in part, in vitro or in situ.

As used herein, "microRNA" or "miRNA" describes small non-coding RNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are generally processed from hairpin precursors of about 70 or more nucleotides (pre-miRNA) which are derived from primary transcripts (pri-miRNA) through sequential cleavage by RNAse III enzymes. miRBase is a comprehensive microRNA database located at www.mirbase.org. In general, miRNA genes are transcribed into a precursor or pre miRNA that is processed into mature miRNA. pre-miRNA generally occurs in a hairpin form, wherein the hairpin contains a 5' arm (or side) connected to a loop that is then connected to a 3' arm (or side). Processing of the precursor miRNA can result in the formation of two mature forms of miRNA, including a 5p form that is derived from the 5' side or arm of the precursor miRNA loop and a 3p form that is derived from the 3' side or arm of the precursor miRNA hairpin.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

As used herein, the term "a" may refer to a singular of plural form. In other words, "a" generally refers to "one or more." Similarly, the term "an" may refer to a singular or plural form.

As used herein, RNA and RNAs are used interchangeably and may refer to a singular RNA or multiple RNA. Similarly, miRNA and miRNAs are used interchangeably and may refer to a singular miRNA or multiple miRNA.

As used herein, "non-coding RNA" (ncRNA) generally refers to an endogenous RNA molecule that is not translated into a protein in a cell. Exemplary types of ncRNAs include transfer RNAs (tRNAs), ribosomal RNAs (rRNAs), microRNAs (miRNAs), piRNAs, snoRNAs, snRNAs, exRNAs, scRNAs and long ncRNAs (such as Xist and HOTAIR). In some embodiments, testing for endometriosis as described herein may involve determining the level of one or more ncRNA that is not a miRNA in addition to the specific microRNAs described herein.

As used herein, the term "random forest" refers to an ensemble learning method for classification, regression and other tasks that operates by constructing a multitude of decision trees at training time and outputting the class that is the mode of the classes (classification) or mean prediction (regression) of the individual trees. Implementation of random forest for data classification has been described in a variety of contexts.

As used herein, the term "support-vector machine" (SVM) refers to a supervised learning method that analyzes data used for classification and regression analysis. Given a set of training examples, each marked as belonging to one or the other of two categories, an SVM training algorithm builds a model that assigns new examples to one category or the other, making it a non-probabilistic binary linear classifier (although methods such as Platt scaling exist to use SVM in a probabilistic classification setting). An SVM model is a representation of the examples as points in space, mapped so that the examples of the separate categories are divided by a clear gap that is as wide as possible. New examples are then mapped into that same space and predicted to belong to a category based on the side of the gap on which they fall.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced.

The terms "adaptor(s)", "adapter(s)" may be used synonymously. An adaptor or tag can be coupled to a polynucleotide sequence by any approach, including ligation, hybridization, primer extension, or other approaches. Adaptors or tags may be added to a nucleic acid to facilitate attachment to a sequencing flow cell, to facilitate binding of sequencing primers to a nucleic acid, or for counting individual copies of a nucleic acid sequence in a mixture (e.g., used as a unique molecular identifier).

In various embodiments, the amount of a target analyte may be normalized to a normalizer control using the "delta CT method" or "ΔCT method," which involves calculating the ΔCT. In certain embodiments, the ΔCT is calculated by subtracting the CT (cycle threshold) of a quantitative nucleic acid detection assay (e.g., a qPCR assay) used to detect a normalizer control from the CT of a quantitative nucleic acid detection assay (e.g., a qPCR assay) used to detect a target analyte. In certain embodiments, the fold difference in the amounts of the normalizer control and target analyte is calculated from the ΔCT—In certain embodiments, the fold difference in the amounts of the normalizer control and target analyte is calculated from the ΔCT according to the formula $2^{-\Delta CT}$. In some embodiments, the normalizer control is a housekeeping nucleic acids (e.g., DNA or RNA encoding a housekeeping polypeptide. In some cases, the normalizer control is small nuclear RNA gene U6.

Subjects

The methods and compositions described herein are applicable to human and non-human subjects, including veterinary subjects. Preferred subjects are "patients"—living humans that are receiving medical care for a disease or condition (e.g., endometriosis), or who are suspected of having such disease or condition or who are at risk of having such disease or condition. This includes persons with no defined illness who are being investigated for signs of pathology (e.g., endometriosis).

Preferred patients or subjects for the methods and compositions described herein are female patients that are at pubescent or post-pubescent ages, pre-menopausal, peri-menopausal, menopausal, or post-menopausal (as endometriosis may persist after menopause). As such, in general, the methods and compositions provided herein may be useful for female subjects within a large range of ages, generally over the age of 10 or over the age of 18. Often, the subject is under the age of 49. In some cases, the subject is premenopausal. In some cases, the subject is premenopausal and over 18. In some cases, the subject is premenopausal and under 49. The subject may be at any phase of the menstrual cycle, e.g., luteal or proliferative.

In some cases, a subject may be at risk of having endometriosis. A subject at risk of having endometriosis, may, for example, have a family history of endometriosis, symptoms of endometriosis, or a past medical history of endometriosis. The endometriosis may be any stage of endometriosis. In some cases, the subject has, or is suspected of having, Stage I, II, III, or IV endometriosis. In some cases, the subject has, or is suspected of having, endometrioma. In some cases, the subject has endometriosis at any stage (e.g., Stage I-IV) but a method provided herein detects endometriosis as a general condition in the subject, without specifying the stage. In some cases, the subject has early stage endometriosis. In some cases, the subject as Stage I/II endometriosis. In some cases, the subject has Stage III/IV endometriosis.

In some cases, a subject may be suspected of having endometriosis. Such a subject may display no symptoms of endometriosis. But in other cases, such subject may display symptoms of endometriosis such as dysmenorrhea, pain with bowel movements or urination, deep dyspareunia, chronic lower abdominal pain, chronic lower back pain, adnexal masses, infertility, or excessive bleeding. In some cases, the subject may be suspected of having endometriosis due to the results of a previous or concurrent test for endometriosis. In some cases, a subject is suspected of having endometriosis due to multiple factors. For example, the subject may be suspected of having endometriosis due to the presence of symptoms in an overall clinical context consistent with endometriosis.

In some cases, a subject may have, or be suspected of having, a non-endometriosis condition. In general, as used herein, the term "non-endometriosis condition" refers to an abnormal reproductive condition that is not endometriosis. Nonlimiting examples of a non-endometriosis condition include fibroids, leiomyomas, cysts, dermoid cysts, serous cystadenomas, cystadenomas, ovarian cysts, mucous cystadenomas, pelvic infection, teratoma, and/or paratubal cysts. In some cases, such subject may display symptoms of endometriosis such as dysmenorrhea, pain with bowel movements or urination, deep dyspareunia, chronic lower abdominal pain, chronic lower back pain, adnexal masses, infertility, or excessive bleeding. In some cases, the non-endometriosis condition is benign. In some cases, the non-endometriosis condition is malignant.

In some cases, the subject may be receiving a hormonal treatment. The hormonal treatment may include GnRH (gonadotrophin releasing hormone) agonists (with or without estrogen/progesterone replacement therapy or tibolone treatment) and antagonists, levonorgestrel-releasing intra-uterine devices (e.g., Mirena), danazol, antiprogesterones, gestrinone, aromatase inhibitors, selective estrogen receptor modulators (SERMs), or selective progesterone receptor modulators (SPRMs).

Samples

The sample is preferably a bodily fluid sample. The bodily fluid may be sweat, saliva, tears, urine, blood, plasma, serum, vaginal fluid, cervico-vaginal fluid, whole blood, menstrual effluent (e.g., menstrual blood), spinal fluid, pulmonary fluid, sputum, or any other bodily fluid. In preferred embodiments, the sample is a saliva or menstrual effluent (e.g., menstrual blood) sample. In some cases, the sample comprises white blood cells (WBCs). In some embodiments, the sample is a plasma sample. In some embodiments, the sample is a cell-free or acellular blood, plasma, or serum sample. In some embodiments, the sample is a blood sample collected by venipuncture into a collection tube without additives (e.g., without anticoagulants or coagulants), followed by centrifugation (e.g., at 2500×g) to remove cells. In some cases, the sample (e.g., blood, serum, plasma, etc.) is subjected to centrifugation, filtration, fractionation, or other method In some cases, the sample comprises peripheral blood mononuclear cells (PBMCs); in some cases, the sample comprises peripheral blood lymphocytes (PBLs). As used herein, the term "saliva" does not include sputum, since sputum pertains to mucus or phlegm samples. In some embodiments, the saliva, peripheral blood sample or menstrual effluent (e.g., menstrual blood) may be separated into cellular and non-cellular fractions by suitable methods (e.g., centrifugation, filtration). In some embodiments, nucleic acids (e.g., miRNA or ncRNA) may be extracted from the cellular (e.g., cell-containing) or non-cellular (e.g., non cell-containing) fractions. In some embodiments, analysis as described herein of miRNA or ncRNA expression may be performed on the cell-containing or non-cellular fractions of any of the samples (e.g., blood, plasma, serum, saliva, menstrual blood, menstrual effluent, etc.).

In some cases, the sample comprises tissue, such as tissue from a biopsy. In some cases, the tissue is endometrial tissue.

In some embodiments, the sample comprises cell-free non-coding RNA (e.g., cell-free miRNA). In some cases, the sample comprises purified or extracted non-coding RNA (e.g., miRNA). In some embodiments, the sample comprises exosome-encapsulated non-coding RNA (e.g., miRNA). In some embodiments, the sample comprises cell-encapsulated (e.g., by white blood cells) non-coding RNA (e.g., miRNA).

Sample Collection

As used herein "obtaining a sample" includes obtaining a sample directly or indirectly, including having a sample obtained (e.g., from a third party who directly obtained the sample from the subject). In some embodiments, the sample is taken from the subject by the same party (e.g., a testing laboratory) that subsequently acquires biomarker data from the sample. In some embodiments, the sample is received (e.g., by a testing laboratory) from another entity that collected it from the subject (e.g., a physician, nurse, phlebotomist, or other medical care provider). In some embodiments, the sample is taken from the subject by a medical professional under direction of a separate entity (e.g., a testing laboratory) and subsequently provided to said entity (e.g., the testing laboratory). In some embodiments, the sample is taken by the subject or the subject's caregiver (e.g., family member, home health aide) at home and subsequently provided to the party that acquires biomarker data from the sample (e.g., a testing laboratory).

In some embodiments, test samples of blood may be obtained from a subject. In some embodiments, the blood sample is a peripheral blood sample. In some embodiments, the blood sample is a whole blood sample. In some embodiments, the sample is a blood sample and comprises whole blood, peripheral blood, serum, plasma, PBLs, PBMCs, T cells, CD4 T cells, CD8 T cells, or macrophages. The blood sample may be obtained by a minimally-invasive method such as a blood draw. The blood sample may be obtained by venipuncture.

In some embodiments, test samples of saliva may be obtained from a subject. Methods of obtaining saliva samples may include, but are not limited to ejection from the subject's mouth (e.g., spitting), aspiration, or removal by a swab or other collection tool. Methods for extracting RNA molecules from saliva can be found in e.g., Pandit, P et al. Clin Chem. 2013 July; 59(7):1118-22. A wide variety of saliva collection and recovery devices (which collect the sample in a clean manner and provide for the stabilization of nucleic acids in the sample) are available as kits and available from commercial providers such as DNA Genotek (e.g., Oragene-RNA and products described in US20110212002A1 and WO2008040126A1) and Norgen Biotek, and are suitable for use with the methods of the disclosure. Such kits are suitable for use by patients individually or with minimal assistance from a medical care provider (e.g., physician).

After collection, the sample (e.g., saliva) sample may be stabilized by the addition of antimicrobial agents (e.g., Normocin, sodium azide), RNase inhibitors (e.g., Polyvinylsulfonic acid, RNasin®, RNaseOUT™), by disruption in organic solution (e.g., Trizol, phenol-chloroform, phenol-chloroform-isoamyl alcohol), or by disruption in detergents in combination with broad-spectrum proteases (e.g., SDS with Proteinase K).

RNA (e.g., miRNA) Expression Profiling

The methods, kits, and systems disclosed herein may comprise specifically detecting, profiling, or quantitating RNAs (e.g., ncRNAs, miRNAs) that are within the biological samples to determine an expression profile. In some instances, RNAs (e.g., miRNAs, ncRNAs) may be isolated from the biological samples. In some cases, RNAs (e.g., miRNAs, ncRNAs) may be isolated from a cell-free source.

In some cases, expression levels are determined by a hybridization-based method, such as Northern blot, Southern blot, molecular beacon, molecular inversion probe, or microarray hybridization. In some cases, the hybridization-based method involves hybridization of a probe to a target RNA (e.g., ncRNA, miRNA), or hybridization of multiple different probes to different target RNAs (e.g., ncRNAs, miRNAs)

In some cases, expression levels are determined by an amplification process or by polymerase chain reaction (PCR). In some cases, expression levels are determined by quantitative PCR, real-time PCR, reverse-transcriptase PCR, or other type of PCR. The PCR may include use of a probe, such as a TaqMan probe.

In some cases, the expression levels are determined by sequencing. Examples of sequencing may include Sanger sequencing, high-throughput sequencing, pyrosequencing, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, Maxim-Gilbert sequencing, primer walking, or any combination thereof. In some embodiments, sequencing may first involve a reverse-transcriptase and/or PCR amplification step to increase abundance of miRNAs to be analyzed or to add appropriate sequencing adaptors. Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Examples of sequencing may include Sanger sequencing, Next Generation sequencing, and RNA sequencing.

Biomarker RNAs (e.g., miRNA, ncRNA)

The methods and compositions herein may involve the detection of one or more ncRNA (e.g., miRNA) associated with endometriosis (e.g., detection of presence or absence of the at least one ncRNA) or measurement of a level one or more miRNA or ncRNA associated with endometriosis from a patient sample to detect, predict, or monitor the severity of endometriosis. In some cases, the detection of the more than one miRNAs further comprises applying a trained algorithm to the expression levels of the more than one miRNA or ncRNA associated with endometriosis. Trained algorithms suitable for application comprise any of the classification algorithms described herein. In some cases, the trained algorithm is a machine learning algorithm. In some cases the machine learning algorithm is a random forest algorithm, k-nearest-neighbors algorithm (KNN), support vector machine (SVM), and Naive Bayes.

In some cases, the classifier set of miRNAs used comprises at least one of miR-125b, miR-150, miR-342, miR-3613, miR-451a, and let-7b, in any number or combination. In some cases, the classifier set of miRNAs used is miR-342, miR-451, and miR-3613. In some cases, the classifier set of miRNAs used is miR-342, miR-451, miR-3613, and miR-125. In some cases, the classifier set of miRNAs used is miR-342, miR-451, miR-3613, miR-125, and let-7. In some cases, the classifier set of miRNAs used is miR-342, miR-451, let-7, and miR-125. In some cases, the classifier set of miRNAs used is miR-342, miR-451, let-7, and miR-3613. In some cases, the classifier set of miRNAs used is miR-342, miR-451, and let-7. In some cases, the classifier set of miRNAs used is miR-125, miR-150, miR-342, miR-451, and let-7. In some cases, the classifier set of miRNAs used is miR-125, miR-150, miR-342, miR-3613, miR-451, and let-7. In some cases, the classifier set of miRNAs used is miR-342, miR-451a, and miR-3613. In some cases, the classifier set of miRNAs used is miR-342, miR-451a, miR-3613, and miR-125b. In some cases, the classifier set of miRNAs used is miR-342, miR-451a, miR-3613, miR-125b, and let-7b. In some cases, the classifier set of miRNAs used is miR-342, miR-451a, let-7b, and miR-125b. In some cases, the classifier set of miRNAs used is miR-342, miR-451a, let-7b, and miR-3613. In some cases, the classifier set of miRNAs used is miR-342, miR-451a, and let-7b. In some cases, the classifier set of miRNAs used is miR-125b, miR-150, miR-342, miR-451a, and let-7b. In some cases, the classifier set of miRNAs used is miR-125b, miR-150, miR-342, miR-3613, miR-451a, and let-7b. In some cases, the classifier set of miRNAs used is miR-342-3p, miR-451a, and miR-3613-5p. In some cases, the classifier set of miRNAs used is miR-342-3p, miR-451a, miR-3613-5p, and miR-125b-5p. In some cases, the classifier set of miRNAs used is miR-342-3p, miR-451a, miR-3613-5p, miR-125b-5p, and let-7b-5p. In some cases, the classifier set of miRNAs used is miR-342-3p, miR-451a, let-7b-5p, and miR-125b-5p. In some cases, the classifier set of miRNAs used is miR-342-3p, miR-451a, let-7b-5p, and miR-3613-5p. In some cases, the classifier set of miRNAs used is miR-342-3p, miR-451a, and let-7b-5p. In some cases, the classifier set of miRNAs used is miR-125b-5p, miR-150-5p, miR-342-3p, miR-451a, and let-7b-5p. In some cases, the classifier set of miRNAs used is miR-125b-5p, miR-150-5p, miR-342-3p, miR-3613-5p, miR-451a, and let-7b-5p.

Treatment

In some embodiments, the methods of the present disclosure include assigning or administering treatment to a patient having, at risk of developing, or suspected of having endometriosis. By detecting the clinical status of the patient using the classifiers or miRNAs described herein, the appropriate treatment can be assigned or administered to a patient suffering from endometriosis. These treatments can include, but are not limited to, hormone therapy, chemotherapy, immunotherapy, and surgical treatment. Similarly, the methods of the current disclosure can be used to assign or administer treatment to a patient with reduced fertility due to endometriosis. In this fashion, by determining the degree to which the patient's fertility has been reduced, through the detection of biomarkers found herein, the appropriate treatment can be assigned or administered. Relevant treatments include, but are not limited to, hormone therapy, chemotherapy, immunotherapy, and surgical treatment.

In some embodiments, the level of one or more miRNA (e.g., circulating miRNAs) or a classifier outputting a clinical condition determined therefrom in a biological sample of a patient is used to detect, diagnose, monitor, or prognose disease (e.g., endometriosis) in the patient. In some embodiments, the level of one or more miRNAs (e.g., circulating miRNA) in a test sample obtained from a patient can be compared to the level from a reference sample obtained from that patient at a prior timepoint. In some cases, the patient is clinically monitored; and the patient may, in some cases, serve as her own baseline control. For example, a change in level of one or more miRNAs (e.g., circulating miRNA), either increasing or decreasing, may indicate the development of endometriosis in the patient. In some embodiments, test samples are obtained at multiple time points. In these embodiments, measurement of the level of one or more miRNAs (e.g., circulating miRNA) in the test samples provides an indication of whether the patient has, or is at risk of having endometriosis. In some cases, the level of one or more miRNAs (e.g., circulating miRNA) in a test sample obtained from a patient is compared to the level from a reference sample from a different patient, or a composite or average of different patients.

In some embodiments, the level of one or more circulating miRNAs (or a classifier outputting a clinical condition determined therefrom) in a biological sample of a patient is used to monitor the effectiveness of treatment or the prognosis of disease. In some embodiments, the level of one or more miRNAs (e.g., circulating miRNA) in a test sample obtained from a treated patient can be compared to the level from a reference sample obtained from that patient prior to initiation of a treatment. Clinical monitoring of treatment typically entails that a patient serve as his or her own baseline control. In some embodiments, test samples are obtained at multiple time points following administration of the treatment. In these embodiments, measurement of the level of one or more one or more miRNAs (e.g., circulating miRNA) in the test samples provides an indication of the extent and duration of an in vivo effect of the treatment. In some cases, the level of one or more miRNAs (e.g., circulating miRNA) in a test sample obtained from a treated patient is compared to the level from a reference sample from a different patient, or a composite or average of different patients.

Measurement of biomarker levels (or classification status) may allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

In some embodiments, the disclosure provides a method for monitoring the levels of miRNAs (or clinical condition, such as endometriosis or non-endometriosis) in response to treatment. For example, in certain embodiments, the disclosure provides for a method of determining the efficacy of treatment in a subject, by measuring the levels of one or more miRNAs described herein. In some embodiments, the level of the one or more miRNAs can be measured over time, where the level at one timepoint after the initiation of treatment is compared to the level at another timepoint after the initiation of treatment. In some embodiments, the level of the one or more miRNAs can be measured over time, where the level at one timepoint after the initiation of treatment is compared to the level prior to the initiation of treatment.

The present disclosure provides therapies (e.g., drug, surgical) for the treatment or prevention of endometriosis. A non-limitative list of known methods and materials for endometriosis treatment include, but are not limited to, pain killers, hormonal treatments, chemotherapy, and surgical treatments. In some cases, a patient or subject in which endometriosis is detected by a method provided herein, may undergo additional tests or procedures to confirm the endometriosis. For example, the patient or subject may have surgery (e.g., laparoscopic surgery) to further diagnose or characterize the endometriosis, e.g., the stage of endometriosis; or to treat the endometriosis. Pain killers used for the treatment of endometriosis include both simple analgesics, such as paracetamol, COX-2 inhibitors, aspirin, and other non-steroidal anti-inflammatory drugs well known in the art, and narcotic analgesics, such as morphine, codeine, oxycodone, and others well known in the art. Hormonal treatments include, but are not limited to, oral contraceptives, progestins (such as Dydrogesterone, Medroxyprogesterone acetate, Depot medroxyprogesterone acetate, Norethisterone, Levonorgestrel), progesterone and progesterone-like substances, GnRH agonists (such as leuprorelin, buserelin, goserelin, histrelin, deslorelin, nafarelin, and triptorelin), androgens and synthetic androgens like Danazol, GnRH agonists (e.g., Elagolix) (with or without estrogen/progesterone replacement therapy or tibolone treatment), levonorgestrel-releasing intrauterine devices (e.g., Mirena), danazol, antiprogesterones, gestrinone, selective estrogen receptor modulators (SERMs), or selective progesterone receptor modulators (SPRMs), and aromatase inhibitors. Surgical treatments include, but are not limited to, laparoscopic surgery, hysterectomy, and oophorectomy. Other treatments particularly well suited for use in the present disclosure are well known in the art. In some embodiments, the patient can be treated using a statin, including but not limited to, atorvastatin, cerivastatin, fluvastatin, lovastatin, mevastatin, pitavastatin, pravastatin, rosuvastatin and simvastatin.

The present disclosure provides therapies (e.g., drugs, surgery) for the treatment or prevention of a non-endometriosis condition. A non-limitative list of known methods and materials for non-endometriosis treatment include, but are not limited to, pain killers, antibiotics, chemotherapy, and surgical treatments. Pain killers may include both simple analgesics, such as paracetamol, COX-2 inhibitors, aspirin, and other non-steroidal anti-inflammatory drugs well known in the art, and narcotic analgesics, such as morphine, codeine, oxycodone, and others well known in the art. Surgical treatments include, but are not limited to, laparoscopic surgery, hysterectomy, and oophorectomy. In some cases, the patient or subject may undergo additional testing or monitoring following a negative result from an endometriosis test or assay described herein. Such subject or patient may, for example, be tested for a non-endometriosis disease or condition e.g., cancer, benign cyst, fibroids, etc. In some cases, following a negative results, the subject or patient may wait a reasonable amount of time (e.g., more than a week, more than a month, more than 6 months) and be tested again for endometriosis. In some cases, such testing may be by a method provided herein. In some cases, in response to a negative endometriosis result, the subject or patient may avoid undergoing a surgical intervention (e.g., laparoscopic surgery).

Sample Classification miRNA presence and/or expression data (e.g., data representing the presence or absence or level of particular miRNA from a sample from a patient) according to methods of the disclosure can be used to classify a sample. For example, a sample can be classified as, or predicted to be: a) from a patient having endometriosis or b) from a patient not having endometriosis. Many statistical classification techniques are suitable as approaches to perform such a classification. In supervised learning approaches, a group of samples from two or more groups (e.g., endometriosis or not) are analyzed or processed with a statistical classification method. miRNA absence/presence or expression level can be used as a basis for classifier that differentiates between the two or more groups. A new sample can then be analyzed or processed so that the classifier can associate the new sample with one of the two or more groups. Commonly used supervised classifiers include without limitation the neural network (multi-layer perceptron), support vector machines, k-nearest neighbours, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers for use with methods according to the disclosure include quadratic classifiers, k-nearest neighbor, boosting, decision trees, random forests, neural networks, pattern recognition, Bayesian networks and Hidden Markov models. Other classifiers, including improvements or combinations of any of these, commonly used for supervised learning, can also be suitable for use with the methods described herein.

Classification using supervised methods is generally performed by the following methodology:

1. Gather a training set. These can include, for example, expression levels of one or more miRNAs described herein from a sample from a patient having endometriosis or expression levels of one or more miRNAs described herein from a sample from a patient not having endometriosis. The training samples are used to "train" the classifier.

2. Determine the input "feature" representation of the learned function. The accuracy of the learned function depends on how the input object is represented. Typically, the input object is transformed into a feature vector, which contains a number of features that are descriptive of the object. The features might include a set of miRNAs detected in a sample from a patient or subject.

3. Determine the structure of the learned function and corresponding learning algorithm. A learning algorithm is chosen, e.g., artificial neural networks, decision trees, Bayes classifiers or support vector machines. The learning algorithm is used to build the classifier.

4. Build the classifier (e.g., classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set. The built model can involve feature coefficients or importance measures assigned to individual features.

In some cases, the individual features are miRNA or levels of miRNA. In some cases, the level of miRNA is a normalized value, an average value, a median value, a mean value, an adjusted average, or other adjusted level or value. The individual features may comprise or consist of sets or panels of miRNA, such as the sets provided herein In some cases, the machine learning algorithm has importance measures or feature importances assigned to miRNA features. In some cases, the importance measures or feature importances are predetermined; for example, the importance measure may have been arrived at via training on a previous data set. In some cases, the importance measure assigned to miR-342 is greater than importance measures or feature importances assigned to one or more additional miRNA (e.g., miR-150, miR-3613, miR-451a, let-7b, or miR-125b, or other miRNA associated with endometriosis). In some cases, the importance measure assigned to miR-451a is greater than the importance measure assigned to one or more of miR-3613, miR-125b, or let-7b.

In some embodiments, applying a machine learning algorithm (e.g., random forest algorithm) to the expression profile comprises applying a machine learning algorithm with specific importance measures or feature importances assigned to the miRNA features, wherein the importance measure of miR-342 is greater than at least one of miR-150, let-7b, or miR-125. In some embodiments, applying a machine learning algorithm to the expression profile comprises applying a machine learning algorithm with specific importance measures or feature importances assigned the miRNA features, wherein the importance measure of miR-125b is greater than at least one of miR-150, let-7b, or miR-125. In some embodiments, the importance measure or feature importance ranking of the miRNA features from highest to lowest is miR-125b, let-7b, miR-2613, miR-150, miR-342, and miR-451a (or any subset thereof). In some embodiments, the importance measure (e.g., feature importance) ranking of the miRNA features from highest to lowest is miR-342, miR-451a, miR-3613, miR-125b, let-7b, and miR-150.

In some embodiments, a machine learning algorithm (e.g., random forest algorithm) is applied to the expression profile of miRNAs derived from a saliva sample. In some embodiments, applying such a machine learning algorithm involves applying a machine learning algorithm with specific importance measures or feature importances assigned to the miRNA features, wherein the importance of miR-125b is greater than at least one of let-7b, miR-3613, miR-150, miR-342, or miR-451a. In some embodiments, applying such a machine learning algorithm involves applying a machine learning algorithm with specific importance measures or feature importances assigned to the miRNA features, wherein the importance measure or feature importance of let-7b is greater than at least one of miR-3613, miR-150, miR-342, or miR-451a. In some embodiments, applying such a machine learning algorithm involves applying a machine learning algorithm with specific importance measures or feature importances assigned to the miRNA features, wherein the importance measure or feature importance of miR-3613 is greater than at least one of miR-150, miR-342, or miR-451a. In some embodiments, applying such a machine learning algorithm involves applying a machine learning algorithm with specific importance measures or feature importances assigned to the miRNA features, wherein the importance measure or feature importance of miR-150 is greater than at least one of miR-342 or miR.451a. In some embodiments, applying such a machine learning algorithm involves applying a machine learning algorithm with specific importance measures or feature importances assigned to the miRNA features, wherein the importance measure or feature importance of miR-342 is greater than miR-451a. In some embodiments, applying such a machine learning algorithm involves applying a machine learning algorithm with specific importance measures or feature importances assigned to the miRNA features, wherein the importance measure or feature importance of miR-451a is less than at least one of miR-341, miR-150, miR-3613, let-7b, or miR-125b. In some embodiments, applying such a machine learning algorithm involves applying a machine learning algorithm with specific importance measures or feature importances assigned to the miRNA features, wherein the importance measure or feature importance of miR-342 is less than at least one of miR-125b, let-7b, miR-3613, or miR-150. In some embodiments, applying such a machine learning algorithm involves applying a machine learning algorithm with specific importance measures or feature importances assigned to the miRNA features, wherein the importance measure or feature importance of miR-150 is less than at less than at least one of miR-3613, let-7b, or miR-125b. In some embodiments, applying such a machine learning algorithm involves applying a machine learning algorithm with specific importance measures or feature importances assigned to the miRNA features, wherein the importance measure or feature importance of miR3613 is less than miR-125b or let-7b. In some embodiments, applying such a machine learning algorithm involves applying a machine learning algorithm with specific importance measures or feature importances assigned to the miRNA features, wherein the importance measure or feature importance of let7b is less than miR-125b. In some embodiments, applying such a machine learning algorithm involves applying a machine learning algorithm with specific importance measures or feature importances assigned to the miRNA features, wherein the importance measure or feature importance of miRNAs is in order miR-125b, let-7b, miR-3613, miR-150, miR-342, and miR-451a.

In some embodiments, a machine learning algorithm (e.g., random forest algorithm) is applied to the expression profile of miRNAs derived from a sample (e.g., serum sample). In some embodiments, applying such a machine learning algorithm involves applying a machine learning algorithm that has importance measures or feature importances assigned to particular miRNA features, wherein the importance measure or feature importance of miR-342 is greater than at least one of miR-125b, miR-451a, miR-3613, miR-150, or let-7b. In some embodiments, the importance measure or feature importance of miR-125b is greater than at least one of miR-451a, miR-3613, miR-150, or let-7b. In some embodiments, the importance measure or feature importance of miR-451a is greater than at least one of miR3613, miR-150, or let-7b. In some embodiments, the importance measure or feature importance of miR-3613 is greater than miR-150 or let-7b. In some embodiments, the importance measure or feature importance of miR-150 is greater than let-7b. In some embodiments, the importance measure or feature importance of let-7b is less than at least one of miR-150, miR-3613, miR-451a, miR-125b, or miR-342. In some embodiments, the importance measure or feature importance of miR-150 is less than at least one of miR-3613, miR-451a, miR-125b, or miR-342. In some embodiments, importance measure or feature importance of miR-3613 is less than at least one of miR-451a, miR-125b, or miR-342. In some embodiments, the importance measure or feature importance of miR-451a is less than miR-125b or miR-342. In some embodiments, the importance measure or feature importance of miR-125b is less than miR-342. In some embodiments, the importance measure or feature importance measure or feature importance of miRNAs is in order miR-342, miR-125b, miR-451a, miR-3613, miR-150, and let-7b.

In some embodiments, a machine learning algorithm (e.g., random forest algorithm) is applied to the expression profile of miRNAs derived from a sample (e.g., serum sample). In some embodiments, applying such a machine learning algorithm involves applying a machine learning algorithm with specific importance measures or feature importances assigned to the miRNA features, wherein the importance measure or feature importance of miR-342 is greater than at least one of miR-451a, miR-3613, miR-125b, let-7b, or miR-150. In some embodiments, applying such a machine learning algorithm involves applying a machine learning algorithm with specific importance measures or feature importances assigned to the miRNA features, wherein the importance measure or feature importance of miR-451a is greater than at least one of miR-3613, miR-125b, let-7b, or miR-150. In some embodiments, applying such a machine learning algorithm involves applying a machine learning algorithm with specific importance measures or feature importances assigned to the miRNA features, wherein the importance measure or feature importance of miR-3613 is greater than at least one of miR-125b, let-7b, or miR-150. In some embodiments, applying such a machine learning algorithm involves applying a machine learning algorithm with specific importance measures or feature importances assigned to the miRNA features, wherein the importance measure or feature importance of miR-125b is greater than let-7b or miR-150. In some embodiments, applying such a machine learning algorithm involves applying a machine learning algorithm with specific importance measures or feature importances assigned to the miRNA features, wherein the importance measure or feature importance of let-7b is greater than miR-150. In some embodiments, applying such a machine learning algorithm involves applying a machine learning algorithm with specific importance measures or feature importances assigned to the miRNA features, wherein the importance measure or feature importance of miR-150 is less than at least one of let-7b, miR-125b, miR-3613, miR-451a, or miR-342. In some embodiments, applying such a machine learning algorithm involves applying a machine learning algorithm with specific importance measures or feature importances assigned to the miRNA features, wherein the importance measure or feature importance of let-7b is less than at least one of miR-125b, miR-3613, miR-451a, or miR-342. In some embodiments, applying such a machine learning algorithm involves applying a machine learning algorithm with specific importance measures or feature importances assigned to the miRNA features, wherein the importance measure or feature importance of miR-125b is less than at least one of miR-3613, miR451a, or miR-342. In some embodiments, applying such a machine learning algorithm involves applying a machine learning algorithm with specific importance measures or feature importances assigned to the miRNA features, wherein the importance measure or feature importance of miR-3613 is less than miR-342 or miR-451a. In some embodiments, applying such a machine learning algorithm involves applying a machine learning algorithm with specific importance measures or feature importances assigned to the miRNA features, wherein the importance measure or feature importance of miR-451a is less than miR-342. In some embodiments, applying such a machine learning algorithm involves applying a machine learning algorithm with specific importance measures or feature importances assigned to the miRNA features, wherein the importance measure or feature importance of miRNAs is in order miR-342, miR-451a, miR-3613, miR-125b, let-7b, and miR-150.

In some embodiments, a machine learning algorithm (e.g., random forest algorithm) is applied to the expression profile of miRNAs derived from a sample (e.g., serum sample). In some embodiments, applying such a machine learning algorithm involves applying a machine learning algorithm with specific importance measures or feature importances assigned to the miRNA features, wherein the importance measure or feature importance of miR-125b is greater than at least one of miR-3613, miR-451a, miR-150, miR-342, or let-7b. In some embodiments, applying such a machine learning algorithm involves applying a machine learning algorithm with specific importance measures or feature importances assigned to the miRNA features, wherein the importance measure or feature importance of miR-3613 is greater than at least one of miR-451a, miR-150, miR-342, or let-7b. In some embodiments, applying such a machine learning algorithm involves applying a machine learning algorithm with specific importance measures or feature importances assigned to the miRNA features, wherein the importance measure or feature importance of miR-451 a is greater than at least one of miR-150, miR-342, or let-7b. In some embodiments, applying such a machine learning algorithm involves applying a machine learning algorithm with specific importance measures or feature importances assigned to the miRNA features, wherein the importance measure or feature importance of miR-150 is greater than miR-342 or let-7b. In some embodiments, applying such a machine learning algorithm involves applying a machine learning algorithm with specific importance measures or feature importances assigned to the miRNA features, wherein the importance measure or feature importance of miR-342 is greater than let-7b. In some embodiments, applying such a machine learning algorithm involves applying a machine learning algorithm with specific importance measures or feature importances assigned to the miRNA features, wherein the importance measure or feature importance of let-7b is less than at least one of miR-342, miR-150, miR-451a, miR-3613, or miR-125b. In some embodiments, applying such a machine learning algorithm involves applying a machine learning algorithm with specific importance measures or feature importances assigned to the miRNA features, wherein the importance measure or feature importance of miR-342 is less than at least one of miR-150, miR-451a, miR-3613, or miR-125b. In some embodiments, applying such a machine learning algorithm involves applying a machine learning algorithm with specific importance measures or feature importances assigned to the miRNA features, wherein the importance measure or feature importance of miR-150 is greater than at least one of miR-451a, miR-3613, or miR-125b. In some embodiments, applying such a machine learning algorithm involves applying a machine learning algorithm with specific importance measures or feature importances assigned to the miRNA features, wherein the importance measure or feature importance of miR-451a is less than miR-3613 or miR-125b. In some embodiments, applying such a machine learning algorithm involves applying a machine learning algorithm with specific importance measures or feature importances assigned to the miRNA features, wherein the importance measure or feature importance of miR-3613 is less than miR-125b. In some embodiments, applying such a machine learning algorithm involves applying a machine learning algorithm with specific importance measures or feature importances assigned to the miRNA features, wherein the importance measure or feature importance of miRNAs is in order miR-125b, miR-3613, miR-451a, miR-150, miR-342, and let-7b.

Once the classifier (e.g., classification model) is determined as described above ("trained"), it can be used to classify a sample, e.g., a patient sample comprising miRNAs that is analyzed or processed according to methods described herein.

Unsupervised learning approaches can also be used with methods described herein. Clustering is an unsupervised learning approach wherein a clustering algorithm correlates a series of samples without the use the labels. The most similar samples are sorted into "clusters." A new sample could be sorted into a cluster and thereby classified with other members that it most closely associates.

The methods provided herein may include using a trained classifier or algorithm to analyze sample data, particularly to detect endometriosis. In some instances, the levels of RNA (e.g., miRNA, ncRNA) from a sample are used to develop or train an algorithm or classifier provided herein. In some instances, RNA levels (e.g., miRNA, ncRNA levels) are measured in a sample from an asymptomatic patient or a patient having one or more symptom of endometriosis and a classifier or algorithm (e.g., trained algorithm) is applied to the resulting data in order to detect, predict, or monitor endometriosis.

Training of multi-dimensional classifiers (e.g., algorithms) may be performed using numerous samples. For example, training of the multi-dimensional classifier may be performed using at least about 10, 20, 30, 40, 50, 60, 70, 80, 90, 100, 110, 120, 130, 140, 150, 160, 170, 180, 190, 200 or more samples. In some cases, training of the multi-dimensional classifier may be performed using at least about 200, 210, 220, 230, 240, 250, 260, 270, 280, 290, 300, 350, 400, 450, 500 or more samples. In some cases, training of the multi-dimensional classifier may be performed using at least about 525, 550, 600, 650, 700, 750, 800, 850, 900, 950, 1000, 1100, 1200, 1300, 1400, 1500, 1600, 1700, 1800, 2000 or more samples.

Further disclosed herein are classifier sets and methods of producing one or more classifier sets. The classifier set may comprise one or more RNAs (e.g., miRNAs, ncRNA), such as let-7a, let-7b, let-7c, let-7d, let-7e, let-7f, miR-135a, miR-135b, miR-18a, miR-125b, miR-143, miR-145, miR-150, miR-342, miR-451a, miR-500a, miR-3613, and miR-6755 individually or in any combination. In some cases, the classifier set of miRNAs used is miR-342, miR-451a, and miR-3613. In some cases, the classifier set of miRNAs used is miR-342, miR-451a, miR-3613, and miR-125b. In some cases, the classifier set of miRNAs used is miR-342, miR-451a, miR-3613, miR-125b, and let-7b. In some cases, the classifier set of miRNAs used is miR-342, miR-451a, let-7b, and miR-125b. In some cases, the classifier set of miRNAs used is miR-342, miR-451a, let-7b, and miR-3613. In some cases, the classifier set of miRNAs used is miR-342, miR-451a, and let-7b. In some cases, the classifier set of miRNAs used is miR-125b, miR-150, miR-342, miR-451a, and let-7b. In some cases, the classifier set of miRNAs used is miR-125b, miR-150, miR-342, miR-3613, miR-451a, and let-7b.

Classifiers and/or classifier probe sets may be used to either rule-in or rule-out a sample as healthy (e.g., as being derived from a healthy subject). For example, a classifier may be used to classify a sample as being from a healthy subject. Alternatively, a classifier may be used to classify a sample as being from an unhealthy subject (e.g., as being derived from an unhealthy subject). Alternatively, or additionally, classifiers may be used to either rule-in or rule-out a sample as endometriosis (e.g., as being derived from a subject with endometriosis). For example, a classifier may be used to classify a sample as being from a subject suffering from endometriosis. In another example, a classifier may be used to classify a sample as being from a subject that is not suffering from endometriosis.

The methods disclosed herein may comprise assigning a classification to one or more samples from one or more subjects. Assigning the classification to the sample may comprise applying an algorithm to the level of one or more RNA (e.g., miRNA, ncRNA) from the sample.

The algorithm may provide a record of its output including a classification of a sample and/or a confidence level. In some instances, the output of the algorithm can be the possibility of the subject of having a condition, such as endometriosis.

The algorithm may be a trained algorithm. The algorithm may comprise a linear classifier. The linear classifier may comprise one or more linear discriminant analysis, Fisher's linear discriminant, Naïve Bayes classifier, Logistic regression, Perceptron, Support vector machine, or a combination thereof. The linear classifier may be a Support vector machine (SVM) algorithm.

The algorithm may comprise one or more linear discriminant analysis (LDA), Basic perceptron, Elastic Net logistic regression, logistic regression, (Kernel) Support Vector Machines (SVM), Diagonal Linear Discriminant Analysis (DLDA), Golub Classifier, Parzen-based, (kernel) Fisher Discriminant Classifier, k-nearest neighbor, Iterative RELIEF, Classification Tree, Maximum Likelihood Classifier, Random Forest, Nearest Centroid, Prediction Analysis of Microarrays (PAM), k-medians clustering, Fuzzy C-Means Clustering, Gaussian mixture models, or a combination thereof. The algorithm may comprise a Diagonal Linear Discriminant Analysis (DLDA) algorithm. The algorithm may comprise a Nearest Centroid algorithm. The algorithm may comprise a Random Forest algorithm.

The methods provided herein can help determine whether the patient has endometriosis with a high degree of accuracy, sensitivity, and/or specificity. In some cases, the predictive accuracy (e.g., for detecting endometriosis, or for distinguishing endometriosis from non-endometriosis) is greater than 55%, 60%, 65%, 70%, 75%, 80%, 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some embodiments, the predictive accuracy is 100%. In some cases, the sensitivity (e.g., for detecting endometriosis, or for distinguishing endometriosis from non-endometriosis) is greater than 55%, 60%, 65%, 70%, 75%, 80%, 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some embodiments the sensitivity is 100%. In some cases, the specificity (e.g., for detecting endometriosis, or for distinguishing endometriosis from non-endometriosis) is greater than 55%, 60%, 65%, 70%, 75%, 80%, 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some cases, the specificity is 100%. In some cases, the positive predictive value (e.g., for detecting endometriosis, or for distinguishing endometriosis from non-endometriosis) of the method is greater than 55%, 60%, 65%, 70%, 75%, 80%, 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some cases the positive predictive value is 100%. The AUC after thresholding in any of the methods provided herein may be greater than 0.9, 0.91, 0.92, 0.93, 0.94, 0.95, 0.96, 0.97, 0.98, 0.99, 0.995, or 0.999. Conversely, the method may predict or determine whether a subject does not have or is at reduced risk of endometriosis. The negative predictive value (e e.g., for detecting endometriosis, or for distinguishing endometriosis from non-endometriosis) may be greater than 55%, 60%, 65%, 70%, 75%, 80%, 85%, 90%, 91%, 92%, 93%, 94%, 95%, 96%, 97%, 98%, 98.5%, 99.0%, 99.1%, 99.2%, 99.3%, 99.4%, 99.5%, 99.6%, 99.7%, 99.8%, 99.9%, 99.95%, or 99.99%. In some cases, the negative predictive value is substantially equal to 100%.

In some cases, the methods provided herein are optimized for specificity by selecting an optimal cutoff point. The cutoff point may be a threshold or cutoff, above which a sample may be characterized as being from a subject with endometriosis and below which the sample is identified as being from a subject negative for endometriosis. In some situations, the sample is identified as being from a subject positive for endometriosis when below the cutoff, and negative for endometriosis when above the cutoff. In some cases, the cutoff point or threshold is on a receiver operating characteristic (ROC) curve or on a voting percentage distribution. In some cases, the method is optimized to attain a particular specificity, e.g., greater than 80% specificity, greater than 85% specificity, greater than 90% specificity, greater than 95% specificity, greater than 98% specificity. In some cases, the specificity is optimized for a value above the sensitivity of the assay. In some cases, the specificity is optimized to be above a certain value, e.g., above 85%, which may then result in a sensitivity of the assay that is less than a value, e.g., less than 95%, less than 90%, less than 85%, less than 80%. Such assays may be especially suited for non-life threatening conditions, as they may help the subject avoid unnecessary intervention, such as surgical intervention, that can occur when the assay is associated with a high percentage of false positives. In some cases, the method attains a specificity described herein (e.g., greater than 80%, greater than 90%) over a diverse population of women. The population may be a population of over 50 women, over 100 women, over 500 women, over 1000 women, etc. The population may include, for example, women with a range of benign conditions, e.g. cysts, fibroids, leiomyomas, cystadenomas, chronic pelvic infections, teratomas, paratubal cysts.

In some cases, the methods provided herein are optimized for sensitivity by selecting an optimal cutoff point. The cutoff point may be a threshold or cutoff, above which a sample may be characterized as being from a subject with endometriosis and below which the sample is identified as being from a subject negative for endometriosis. In some situations, the sample is identified as being from a subject positive for endometriosis when below the cutoff, and negative for endometriosis when above the cutoff. In some cases, the cutoff point or threshold is on a receiver operating characteristic (ROC) curve or on a voting percentage distribution. In some cases, the method is optimized to attain a particular sensitivity, e.g., greater than 80% sensitivity, greater than 85% sensitivity, greater than 90% sensitivity, greater than 95% sensitivity, greater than 98% sensitivity. In some cases, the sensitivity is optimized for a value above the specificity of the assay. In some cases, the sensitivity is optimized to be above a certain value, e.g., above 85%, which may then result in a specificity of the assay that is less than a value, e.g., less than 95%, less than 90%, less than 85%, less than 80%. Such assays may be especially suited for screening tests for endometriosis. In some cases, the method attains a sensitivity described herein (e.g., greater than 80%, greater than 90%) over a diverse population of women. The population may be a population of over 50 women, over 100 women, over 500 women, over 1000 women, etc. The population may include, for example, women with a range of benign conditions, e.g. cysts, fibroids, leiomyomas, cystadenomas, chronic pelvic infections, teratomas, paratubal cysts.

The methods disclosed herein may comprise assigning a classification to one or more samples from one or more subjects. Assigning the classification to the sample may comprise applying an algorithm to the level of one or more RNA (e.g., miRNA, ncRNA) from the sample.

The algorithm may provide a record of its output including a classification of a sample and/or a confidence level. In some instances, the output of the algorithm can be the possibility of the subject of having a condition, such as endometriosis.

In some aspects, the present disclosure provides for administration of a treatment to the subject to treat the endometriosis detected herein based on the classification generated using the machine learning algorithms described herein. Treatments for endometriosis include, but are not limited to, pain killers (e.g., NSAIDs), hormonal treatments, chemotherapy, and surgical treatments. Pain killers used for the treatment of endometriosis include both simple analgesics, such as paracetamol, COX-2 inhibitors, aspirin, and other non-steroidal anti-inflammatory drugs well known in the art, and narcotic analgesics, such as morphine, codeine, and oxycodone. Hormonal treatments include, but are not limited to, oral contraceptives, progestins, such as Dydrogesterone, Medroxyprogesterone acetate, Depot medroxyprogesterone acetate, Norethisterone, Levonorgestrel, and others well known in the art, progesterone and progesterone-like substances, GnRH agonists, such as leuprorelin, buserelin, goserelin, histrelin, deslorelin, nafarelin, triptorelin, and leuprolin, androgens and synthetic androgens like Danazol, GnRH antagonists, and aromatase inhibitors. Surgical treatments include, but are not limited to, laparoscopic surgery, hysterectomy, and oophorectomy.

In some aspects, a GnRH antagonist is administered to treat the endometriosis detected herein. A variety of antagonists of GnRH suitable for clinical administration, both peptide (goserelin acetate, buserelin, histrelin, deslorelin, nafarelin, and triptorelin, leuproreolin) and non-peptide (Elagolix/ABT-620, NBI-56418, see for e.g., Taylor et al. N Engl J Med. 2017 Jul. 6; 377(1):28-40), are available for second-line treatment of endometriosis in individuals with refractory endometriosis.

In some embodiments, the fluid sample collection and diagnosis described above are performed after a defined period of time (e.g., 1 month, 6 month, or 1 year) and the initial dose of the drug used to treat endometriosis (e.g., any of the hormone analogs or antagonists described herein) is adjusted downward when endometriosis is not detected. In some embodiments, the fluid sample collection and diagnosis described above are performed after a defined period of time (e.g., 1 month, 6 month, or 1 year) and the initial dose of the drug is adjusted upward when endometriosis is detected. In some embodiments, the fluid sample collection and diagnosis described above are performed after a defined period of time (e.g., 1 month, 6 month, or 1 year) and administration of the drug is terminated when endometriosis is not detected.

Computer-Implemented Methods

Expression levels of one or more RNAs (e.g., miRNA, ncRNA) can be analyzed and associated with status of a subject (e.g., endometriosis) in a digital computer. Optionally, such a computer is directly linked to a scanner or the like (e.g., a qPCR system, a multiplex fluorescent plate reader, FACS instrument, or a sequencer) receiving experimentally determined signals related to miRNA or ncRNA expression levels. Alternatively, expression levels can be inputted by other means. The computer can be programmed to convert raw signals into expression levels (absolute or relative), compare measured expression levels with one or more reference expression levels, or a scale of such values, as described above. The computer can also be programmed to assign values or other designations to expression levels based on the comparison with one or more reference expression levels, and to aggregate such values or designations for multiple genes in an expression profile. The computer can also be programmed to output a value or other designation providing an indication of presence of endometriosis as well as any of the raw or intermediate data used in determining such a value or designation.

A typical computer (see U.S. Pat. No. 6,785,613 FIGS. 4 and 5) may include a bus which interconnects major subsystems such as a central processor, a system memory, an input/output controller, an external device such as a printer via a parallel port, a display screen via a display adapter, a serial port, a keyboard, a fixed disk drive and a floppy disk drive operative to receive a floppy disk. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above.

The automated apparatus can include a robotic arm for delivering reagents for determining expression levels, as well as small vessels, e.g., microtiter wells for performing the expression analysis.

The methods, systems, kits, and compositions provided herein may also be capable of generating and transmitting results through a computer network. In some cases, a sample is first collected from a subject (e.g., a patient with one or more symptoms of endometriosis, or a non-symptomatic patient). In some instances, the sample is assayed and RNA (e.g., miRNA, ncRNA) levels are measured. A computer system may be used in analyzing the data and making classification of the sample. The result may be capable of being transmitted to different types of end users via a computer network. In some instances, the subject (e.g., patient) may be able to access the result by using standalone software and/or a web-based application on a local computer capable of accessing the internet. In some instances, the result can be accessed via a mobile application provided to a mobile digital processing device (e.g., mobile phone, tablet, etc.). In some instances, the result may be accessed by medical care provider (e.g., physician) and help them identify and track conditions of their patients. In some instances, the result may be used for other purposes such as education and research.

Computer Program

The methods, kits, and systems disclosed herein may include at least one computer program, or use of the same. A computer program may include a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art may recognize that a computer program may be written in various versions of various languages.

The functionality of the computer readable instructions may be combined or distributed as desired in various environments. The computer program may normally provide a sequence of instructions from one location or a plurality of locations. In various embodiments, a computer program includes, in part or in whole, one or more web applications, one or more mobile applications, one or more standalone applications, one or more web browser plug-ins, extensions, add-ins, or add-ons, or combinations thereof.

Further disclosed herein are systems for classifying one or more samples and uses thereof. The system may comprise (a) a digital processing device comprising an operating system configured to perform executable instructions and a memory device; (b) a computer program including instructions executable by the digital processing device to classify a sample from a subject comprising: (i) a first software module configured to receive a RNA (e.g., miRNA, ncRNA) expression profile of one or more RNA (e.g., miRNA, ncRNA) from the sample from the subject; (ii) a second software module configured to analyze the RNA (e.g., miRNA, ncRNA) expression profile from the subject; and (iii) a third software module configured to classify the sample from the subject based on a classification system comprising two or more classes. At least one of the classes may be selected from endometriosis. Analyzing the gene expression profile from the subject may comprise applying an algorithm. Analyzing the gene expression profile may comprise normalizing the RNA (e.g., miRNA, ncRNA) expression profile from the subject (e.g., to a constitutive RNA such as small nuclear RNA U6, RNU48, RNU44, U47, or RNU6B, or any combination thereof).

Figure 6:
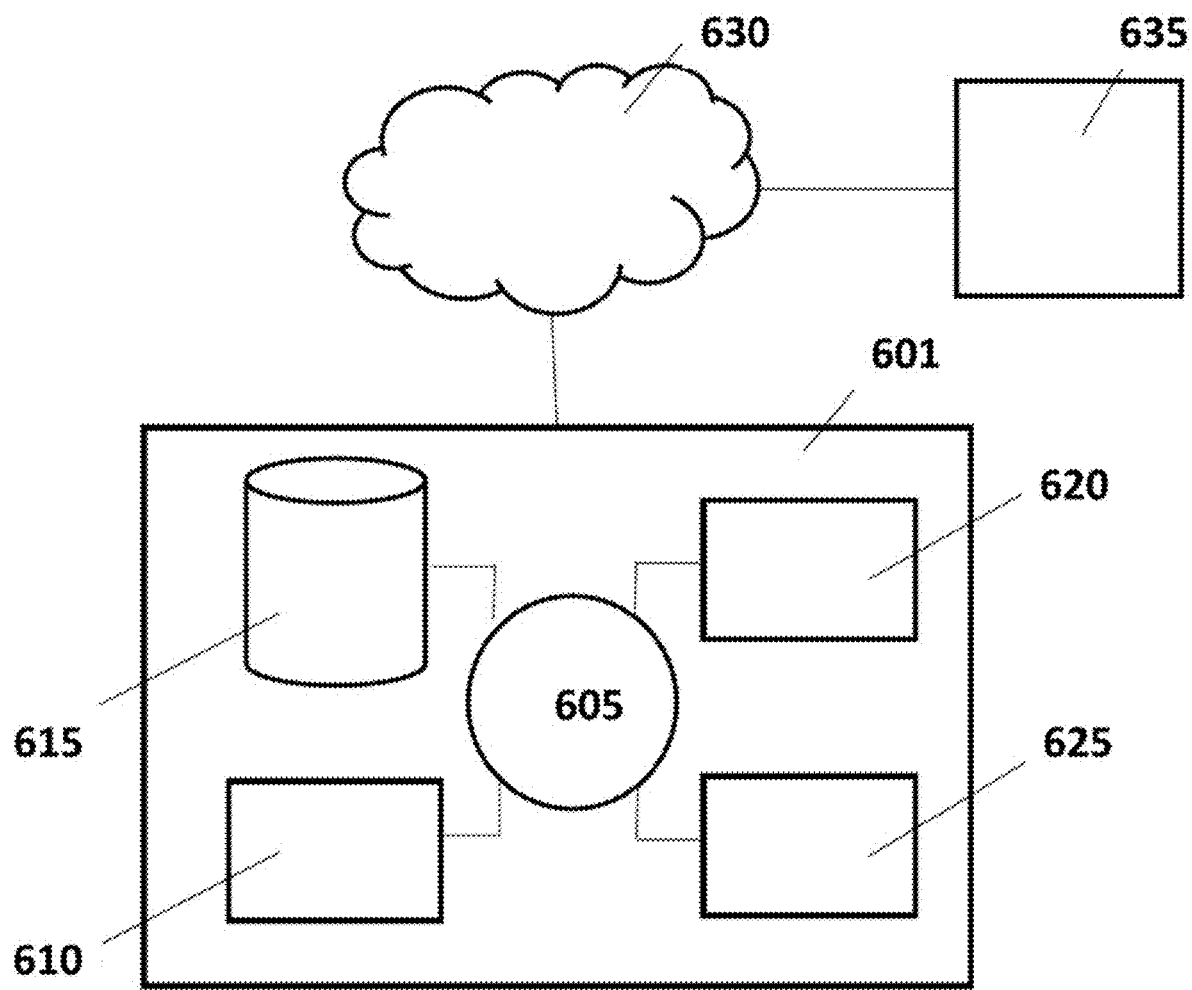
FIG. 6 depicts an example of a computer system for execution of the methods described herein.

FIG. 6 shows a computer system (also "system" herein) 601 programmed or otherwise configured for implementing the methods of the disclosure, such as producing a selector set, and/or for data analysis. The system 601 includes a central processing unit (CPU, also "processor" and "computer processor" herein) 605, which can be a single core or multi core processor, or a plurality of processors for parallel processing. The system 601 also includes memory 610 (e.g., random-access memory, read-only memory, flash memory), electronic storage unit 615 (e.g., hard disk), communications interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communications bus (solid lines), such as a motherboard. The storage unit 615 can be a data storage unit (or data repository) for storing data. The system 601 is operatively coupled to a computer network ("network") 630 with the aid of the communications interface 620. The network 630 can be the Internet, an internet and/or extranet, or an intranet and/or extranet that is in communication with the Internet. The network 630 in some instances is a telecommunication and/or data network. The network 630 can include one or more computer servers, which can enable distributed computing, such as cloud computing. The network 630 in some instances, with the aid of the system 601, can implement a peer-to-peer network, which may enable devices coupled to the system 601 to behave as a client or a server.

The system 601 may be in communication with a processing system 635. The processing system 635 can be configured to implement the methods disclosed herein. In some examples, the processing system 635 is a multiplex fluorescent plate reader, a qPCR machine, or a nucleic acid sequencing system, such as, for example, a next generation sequencing system (e.g., Illumina sequencer, Ion Torrent sequencer, Pacific Biosciences sequencer). The processing system 635 can be in communication with the system 601 through the network 630, or by direct (e.g., wired, wireless) connection. The processing system 635 can be configured for analysis, such as nucleic acid sequence analysis.

Methods as described herein can be implemented by way of machine (or computer processor) executable code (or software) stored on an electronic storage location of the system 601, such as, for example, on the memory 610 or electronic storage unit 615. During use, the code can be executed by the processor 605. In some examples, the code can be retrieved from the storage unit 615 and stored on the memory 610 for ready access by the processor 605. In some situations, the electronic storage unit 615 can be precluded, and machine-executable instructions are stored on memory 610.

Digital Processing Device

The methods, kits, and systems disclosed herein may include a digital processing device or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device may generally include an operating system configured to perform executable instructions. The operating system may be, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The device generally includes a storage and/or memory device. The storage and/or memory device may be one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

A display to send visual information to a user may generally be initialized. Examples of displays include a cathode ray tube (CRT, a liquid crystal display (LCD), a thin film transistor liquid crystal display (TFT-LCD, an organic light emitting diode (OLED) display. In various further embodiments, on OLED display is a passive-matrix OLED (PMOLED) or active-matrix OLED (AMOLED) display. In some embodiments, the display may be a plasma display, a video projector or a combination of devices such as those disclosed herein.

The digital processing device may generally include an input device to receive information from a user. The input device may be, for example, a keyboard, a pointing device including, by way of non-limiting examples, a mouse, trackball, track pad, joystick, game controller, or stylus; a touch screen, or a multi-touch screen, a microphone to capture voice or other sound input, a video camera to capture motion or visual input or a combination of devices such as those disclosed herein.

Non-Transitory Computer Readable Storage Medium

The methods, kits, and systems disclosed herein may include one or more non-transitory computer readable storage media encoded with a program including instructions executable by the operating system to perform and analyze the test described herein; preferably connected to a networked digital processing device. The computer readable storage medium may be a tangible component of a digital that may be optionally removable from the digital processing device. The computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

A non-transitory computer-readable storage media may be encoded with a computer program including instructions executable by a processor to create or use a classification system. The storage media may comprise (a) a database, in a computer memory, of one or more clinical features of two or more control samples, wherein (i) the two or more control samples may be from two or more subjects; and (ii) the two or more control samples may be differentially classified based on a classification system comprising three or more classes; (b) a first software module configured to compare the one or more clinical features of the two or more control samples; and (c) a second software module configured to produce a classifier set based on the comparison of the one or more clinical features.

At least two of the classes may be selected from endometriosis, non-endometriosis, and healthy.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application may be created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not as an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The methods, kits, and systems disclosed herein may include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

The methods, kits, and systems disclosed herein may comprise one or more databases, or use of the same. In view of the disclosure provided herein, those of skill in the art will recognize that many databases are suitable for storage and retrieval of information pertaining to miRNA or ncRNA expression profiles, sequencing data, classifiers, classification systems, therapeutic regimens, or a combination thereof. In various embodiments, suitable databases include, by way of non-limiting examples, relational databases, non-relational databases, object-oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Data Transmission

The methods, kits, and systems disclosed herein may be used to transmit one or more reports. The one or more reports may comprise information pertaining to the classification and/or identification of one or more samples from one or more subjects. The one or more reports may comprise information pertaining to a disease status (e.g., endometriosis or non-endometriosis). The one or more reports may comprise information pertaining to therapeutic regimens for use in treating endometriosis in a subject in need thereof. The one or more reports may be transmitted to a subject or a medical representative of the subject. The medical representative of the subject may be a physician, physician's assistant, nurse, or other medical care provider. The medical representative of the subject may be a family member of the subject. A family member of the subject may be a parent, guardian, child, sibling, aunt, uncle, cousin, or spouse. The medical representative of the subject may be a legal representative of the subject.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1.—Study Population/Patient Selection

Presented herein is a study testing miRNA biomarkers of endometriosis in a more diverse set of patients than previous studies. Serum samples were collected from women prior to undergoing laparoscopy for benign gynecological conditions, and miRNA expression analysis of six target miRNAs was performed without knowledge of surgical findings. This study design enabled testing of whether pre-operative evaluation of these miRNA biomarkers could distinguish endometriosis from other benign conditions, in a diverse patient population consisting of early and late-stage disease.

Institutional Review Board (IRB) approval was obtained from the Yale University School of Medicine (New Haven, Conn.) for biomedical research on human subjects. Written informed consent was obtained from patients admitted to the Yale-New Haven hospital and undergoing laparoscopy or laparotomy for suspected benign indications such as pelvic masses, pelvic pain, infertility and endometriosis. Inclusion criteria were women aged 18-49 years. Exclusion criteria consisted of post-menopausal patients, pregnancy, critical anemia, hyperplasia or polyps, or malignancy. Subjects were stratified into the disease group if visual findings at surgery (and pathology when required), confirmed the presence of endometriosis, and the control group if surgery revealed other benign pathology. All stages of endometriosis as well as untreated and treated subjects were included to provide a full spectrum of disease resulting in varied miRNA levels. Hormonal medications were recorded for each patient. The phase of the menstrual cycle was determined based on the date of the patient's last menstrual period. Staging was done by chart review, using the revised American Society of Reproductive Medicine (rASRM) classification (see Revised American Society for Reproductive Medicine classification of endometriosis: 1996. *Fertility and sterility.* 1997; 67(5):817-821, which is explicitly incorporated by reference herein) by evaluating the surgical comments and pathology results.

Sampling

Between September 2016 and October 2017, serum samples were collected from 103 women who underwent laparoscopic or open gynecologic procedures at Yale New Haven Hospital.

To collect serum samples, prior to surgery (laparoscopic or open), blood (5-10 ml) was drawn from the subjects and collected in sterile tubes (BD, Franklin Lakes, N.J., USA)

without additives. Serum was collected immediately by centrifuging at 2500 rpm for 15 min at 4° C. and stored at −80° C. in 300 μl aliquots.

Among the 103 patients, 3 were excluded due to an unexpected co-morbidity including malignancy on pathology. Of the remaining 100 patients, 41 were categorized as the endometriosis study population and 59 were categorized as the control study population. The endometriosis group was categorized based on visual diagnosis and histological verification of disease. The control group was categorized based on absence of visual disease at time of surgery.

The demographics and clinical characteristics of the study subjects are summarized in Table 1. The mean age of the study population was 34.1±7.1 for the endometriosis group and 36.9±8.2 for the control group. Body mass index was 28.1±7.5 for the endometriosis group and 30.4±7.5 for the control group. There was no statistically significant difference between ages of the women in the two groups (Student's t-test), or between their BMI values (Student's t-test). Study subjects identified predominantly as Caucasian followed by Black/African American and Hispanic.

The endometriosis group consisted of varying degrees of disease as categorized by rASRM stage. The 41 endometriosis subjects were divided into 11 (29%) Stage I, 7 (17%) Stage II, 15 (36%) Stage III, and 8 (19%) Stage IV. Endometriomas were reported in 13 patients. The control group consisted of varying benign pathologies. The 59 control subjects were divided into the following categories: 23 (39%) leiomyomas, 4 (7%) cystadenomas, 5 (8%) chronic pelvic infections, 3 (5%) teratomas, 6 (10%) paratubal cysts, and 18 (31%) without abnormal pathology noted (Table 1).

Phase of menstrual cycle and presence of hormonal medications were recorded and can also be seen in Table 1. In approximately half of the study subjects, the phase of the menstrual cycle could not be accurately determined based on either a history of irregular cycles (data absent) or due to the use of hormonal medication. Of total number of subject including those that could be determined, 8 (19%) were in proliferative phase and 15 (36%) were in secretory phase for the endometriosis group, and 14 (24%) were in proliferative phase and 13 (22%) in secretory phase for the control group. Many study subjects were using hormonal agents at the time of serum collection. For the endometriosis group hormonal agent categories included 10 (24%) combined oral contraception, 5 (12%) progesterone only, 0 (0%) estrogen only, 6 (15%) GnRH agonist, 1 (2%) aromatase inhibitors, and the remaining 19 (46%) were not using any hormonal agent. For the control group hormonal agent categories included 10 (17%) combined oral contraception, 16 (27%) progesterone only, 1 (2%) estrogen only, 5 (8%) GnRH agonist, 1 (2%) aromatase inhibitors, and the remaining 26 (44%) were not using any hormonal agent.

TABLE 1

Patient Demographics and Clinical Characteristics

|  |  | Endometriosis (n = 41) | Control (n = 59) |
|---|---|---|---|
| Age |  | 34.1 ± 7.1 | 36.9 ± 8.2 |
| Body Mass Index (BMI) |  | 28.1 ± 7.5 | 30.4 ± 7.5 |
| Race |  | Number (%) | Number (%) |
|  | Caucasian | 28 (68) | 24 (40) |
|  | Black/African American | 4 (10) | 18 (31) |
|  | Hispanic | 7 (17) | 12 (20) |
|  | Asian | 2 (5) | 2 (3) |
|  | Other | 0 (0) | 3 (5) |
| rASRM Endometriosis Stage |  |  |  |
|  | I | 11 (27) | — |
|  | II | 7 (17) | — |
|  | III | 15 (36) | — |
|  | IV | 8 (19) | — |
| Control Diagnoses |  |  |  |
|  | No abnormality | — | 18 (31) |
|  | Leiomyoma | — | 23 (39) |
|  | Cystadenoma | — | 4 (7) |
|  | Chronic Infection | — | 5 (8) |
|  | Teratoma | — | 3 (5) |
|  | Paratubal Cyst | — | 6 (10) |
| Hormonal Treatment |  |  |  |
|  | Combined OCP | 10 (24) | 10 (17) |
|  | Progesterone | 5 (12) | 16 (27) |
|  | Estrogen | 0 (0) | 1 (2) |
|  | GnRH Agonist | 6 (14) | 5 (8) |
|  | Aromatase Inhibitor | 1 (2) | 1 (2) |
|  | No Treatment | 19 (46) | 26 (44) |
| Phase of Menstrual Cycle |  |  |  |
|  | Proliferative | 8 (19) | 14 (24) |
|  | Secretory | 15 (36) | 13 (22) |
|  | Unable to Determine | 18 (44) | 32 (54) |

Example 2.—MiRNA Expression Analysis From Serum Samples and Saliva Samples

Serum Samples

Total miRNA was extracted from 300 μl of serum sample collected as in Example 1 using the miRNeasy mini Kit from Qiagen (Valencia, Calif., USA) and reverse transcribed using TaqMan Advanced miRNA cDNA synthesis Kit from Applied Biosystems by Life Technologies (Carlsbad, Calif.) according to the manufacturer's specifications. MicroRNA levels were quantified with qRT-PCR using SYBR Green (Bio-Rad Laboratories, Hercules, Calif.) with the MyiQ Single Color Real-Time PCR Detection System (Bio-Rad). The specificity of the amplified transcript and absence of primer-dimers was confirmed by a melting curve analysis. Primers for miRNAs and the U6 gene were obtained from the W. M. Keck Oligonucleotide Synthesis Facility (Yale University, New Haven, Conn.), and universal reverse primer was obtained from Applied Biosystems. Primer sequences were as described in prior studies [40,45] and are listed in Table 2. The following cycling conditions were used in the qRT-PCR reaction: 95° C. for 3 min, 40 cycles of (95° C. for 15 s, 59° C. for 5 s, 72° C. for 55 s). Expression of each miRNA was normalized to the expression of human U6 small nuclear RNA. Relative expression was calculated for each miRNA using the delta (Ct) method, also known as the $2^{-\Delta Ct}$ method. All experiments were carried out at least twice each with duplicate wells run on each plate.

TABLE 2

Exemplary Primer Sequences for miRNA Quantitation

| miRNA | primer | Primer Sequence | SEQ ID NO: | Target RNA sequence | SEQ ID NO: |
|---|---|---|---|---|---|
| Let-7b-5p | forward | TGAGGTAGTAGGTTGTGTGGTT | 1 | UGAGGUAGUAGGUUGUGUGGUU | 8 |
| miR-125b-5p | forward | TCCCTGAGACCCTAACTTGTGA | 2 | UCCCUGAGACCCUAACUUGUGA | 9 |
| miR-150-5p | forward | TCTCCCAACCCTTGTACCAGTG | 3 | UCUCCCAACCCUUGUACCAGUG | 10 |
| miR-342-3p | forward | TCTCACACAGAAATCGCACCCGT | 4 | UCUCACACAGAAAUCGCACCCGU | 11 |
| miR-451a | forward | AAACCGTTACCATTACTGAGTT | 5 | AAACCGUUACCAUUACUGAGUU | 12 |
| miR-3613-5p | forward | TGTTGTACTTTTTTTTTGTTC | 6 | UGUUGUACUUUUUUUUUGUUC | 13 |
| U6 | forward | CTCGCTTCGGCAGCACA | 7 | CUCGCUUCGGCAGCACA | 14 |

Example 3.—Expression Analysis of Individual miRNAs From Serum Samples

In this case-control study, the presence of endometriosis was not known prior to the time of surgery/sample collection, and serum miRNA analysis was performed without knowledge of disease status. The expression levels of six miRNAs (miR-125b-5p, miR-150-5p, miR-342-3p, miR-451a, miR-3613-5p and let-7b) were prospectively measured using quantitative real-time polymerase chain reaction (qRT-PCR) and quantified relative to small nuclear RNA U6. FIG. 1 depicts the average expression levels of these circulating miRNAs in subjects with endometriosis vs. control subjects with other benign gynecologic pathologies. Significantly increased expression was observed of miR-125b, miR-150-5p, miR-342-3p, and miR-451a in patients with endometriosis compared to controls, and significantly reduced expression was observed of miR-3613-5p and let-7b.

Figure 2:
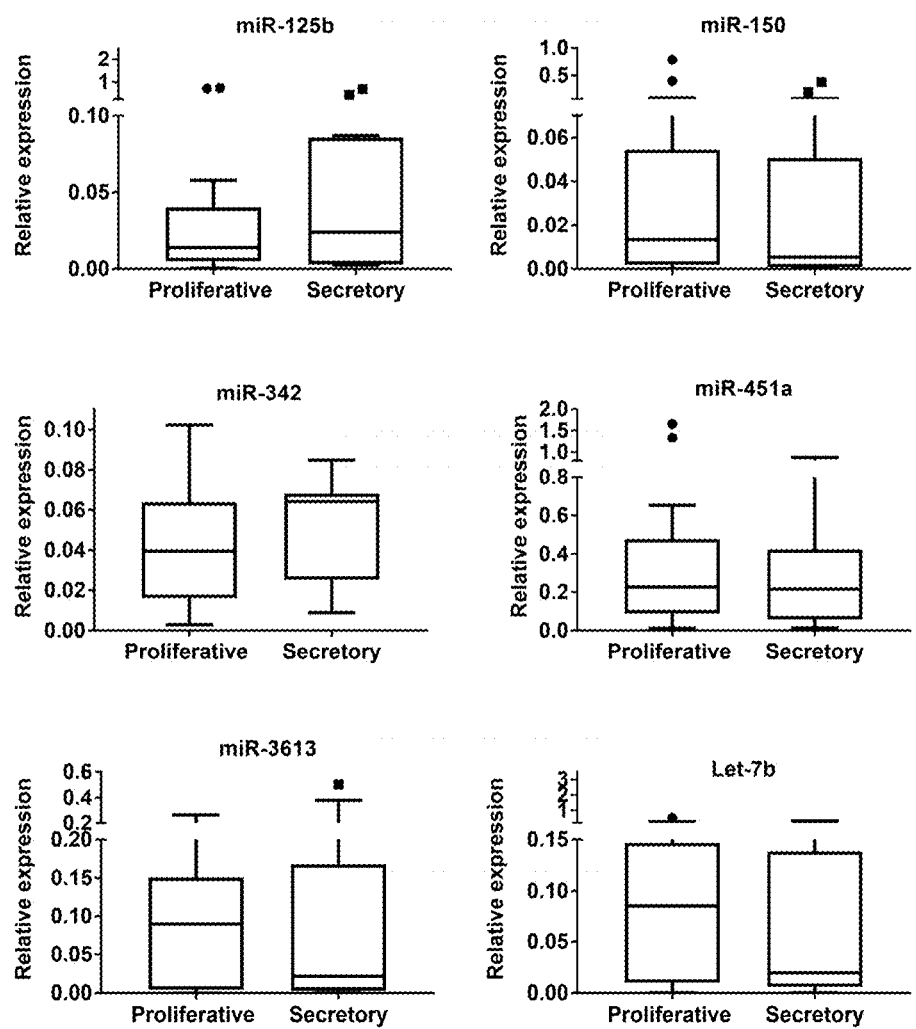
FIG. 2 depicts scatter/box plots of miRNA expression during proliferative or secretory phase, showing that expression of the six miRNAs do not change significantly in proliferative vs secretory phase of the menstrual cycle. Data shows miRNA expression levels in control subjects, separated by phase in menstrual cycle at the time of serum sampling, and normalized relative to levels of the small nuclear RNA gene U6. Data are plotted with the median indicated by a line and the interquartile range (IQR) marked by the box. No significant differences were found (p>0.05, Mann-Whitney U test).

A subgroup analysis was performed to assess whether the timing of serum collection during the menstrual cycle could affect miRNA expression and impact the accuracy of diagnosis with these biomarkers. Control patients were separated based on menstrual phase, no significant difference in expression was observed in miRNA levels between those sampled during the proliferative (14, 24%) vs. secretory (13, 22%) phase (see FIG. 2). When a similar analysis was performed on cycling women identified as having endometriosis, no differences were seen in the average miRNA levels according to phase in the menstrual cycle.

Figure 3:
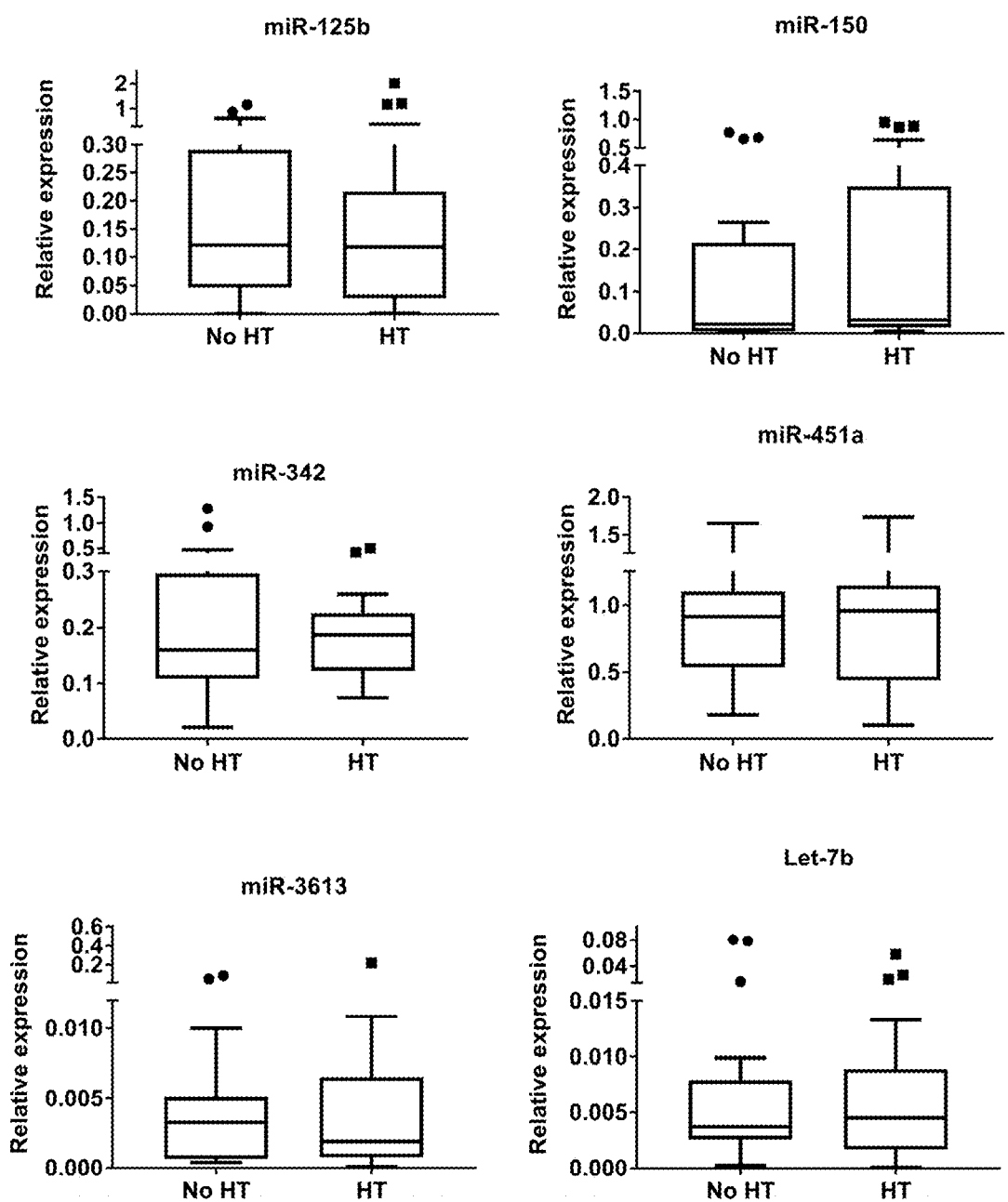
FIG. 3 depicts scatter/box plots of miRNA expression with or without hormonal treatment, demonstrating that the miRNA expression levels do not meaningfully differ depending on hormone-administration status to the subject in the study. Data shows miRNA expression levels in endometriosis subjects, analyzed by presence or absence of hormonal treatment (HT). Levels were normalized relative to levels of the small nuclear RNA gene U6. Data are plotted with the median indicated by a line and the interquartile range (IQR) marked by the box. No significant differences were found (p>0.05, Mann-Whitney U test).

Relative to other studies, this study was designed to reflect a more real-world patient population in terms of demographics and ongoing hormonal therapy. Hormonal therapies were of multiple types (Table 1), with the majority of patients receiving combined oral contraceptives (10, 24%) or GnRH agonists (6, 14%). To determine whether hormonal medications being taken at the time of surgery had any impact on miRNA expression, we analyzed the expression data from endometriosis patients to compare expression of these miRNAs between women who received hormonal treatment (22, 54%) and those that were not on any hormonal medication (19, 46%). As seen in FIG. 3, the presence of hormonal treatment did not significantly affect the average expression levels of the six target miRNAs tested.

Figure 4:
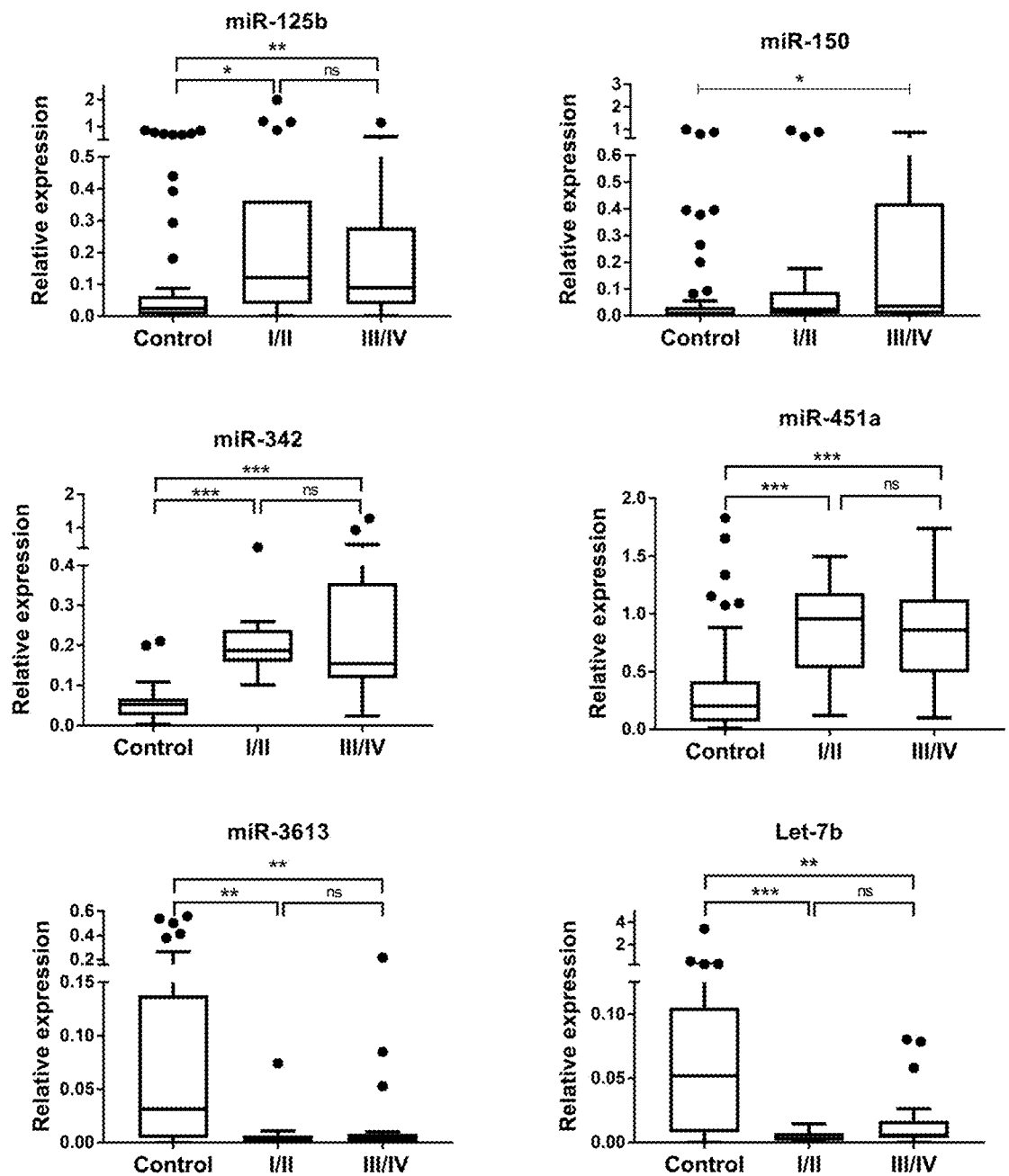
FIG. 4 depicts scatter/box plots of miRNA expression according to rASRM staging, demonstrating that while all markers distinguish between control and severe (III/IV) patients, the ability to distinguish between subsets (e.g., control vs I/II or I/II vs III/IV) varies. Data shows miRNA expression levels in endometriosis subjects, divided by stages of endometriosis: I/II, minimal/mild; III/IV, moderate/severe according to rASRM guidelines. Levels were normalized relative to levels of the small nuclear RNA gene U6. Data are plotted with the median indicated by a line and the interquartile range (IQR) marked by the box. Groups were compared using the Kruskal-Wallis test (a non-parametric one-way ANOVA), and the Dunn's multiple comparisons test was used to compare pairwise means of each subgroup. *p<0.05, p<0.01, *p<0.001.

To evaluate whether expression of these miRNAs correlates with the stage of endometriosis, minimal/mild (Stage I/II) endometriosis was separated from moderate/severe (Stage III/IV) in an analysis. Using a Kruskal-Wallis test (a non-parametric one-way analysis of variance), all six miRNAs were found to have significantly different variances ($p<0.05$) between the three groups: control, Stage I/II, and Stage III/IV (FIG. 4). However, after using Dunn's multiple comparisons test for the three pairwise comparisons, each subgroup of endometriosis had significantly different miRNA levels compared to the control group, but not between minimal/mild vs. moderate/severe (FIG. 4). We also compared the miRNA levels in patients with ovarian endometriosis (endometriomas) compared to those without endometriomas but did not observe any significant differences in this subgroup analysis.

To assess the ability of the individual miRNA expression levels to be used as biomarkers for the presence of endometriosis, receiver operating characteristic (ROC) analysis of each miRNA was carried out. Individual miRNAs had area under the ROC curve (AUC) scores ranging between a low of 0.68 for miR-150-5p up to 0.92 for miR-342-3p (Table 2). For the up-regulated miRNAs (miR-125b-5p, miR-150-5p, miR-342-3p, miR-451a), levels above the cut-off value are indicative of endometriosis, while for the down-regulated miRNAs (let-7b and miR-3613-5p), levels below the cutoff are associated with endometriosis.

TABLE 2

ROC Analysis of Individual miRNAs

| ROC Model | Area (AUC) | Standard Error | 95% Wald Confidence Limits | | Optimal cut-off ($2^{-\Delta CT}$ normalized expression values) | Correct % | Sensitivity % | Specificity % |
|---|---|---|---|---|---|---|---|---|
| miR_125b | 0.73 | 0.05 | 0.63 | 0.83 | 0.084 | 68.0 | 56.1 | 78.0 |
| miR_150 | 0.68 | 0.06 | 0.57 | 0.78 | 0.44 | 63.9 | 20.0 | 94.7 |
| miR_342 | 0.92 | 0.04 | 0.86 | 0.99 | 0.085 | 90.8 | 90.0 | 91.2 |
| miR_451a | 0.84 | 0.04 | 0.76 | 0.92 | 0.35 | 79.8 | 90.0 | 72.9 |
| miR_3613 | 0.76 | 0.05 | 0.66 | 0.85 | 0.014* | 74.0 | 92.7 | 61.0 |
| let_7b | 0.78 | 0.05 | 0.69 | 0.87 | 0.012* | 73.7 | 82.5 | 67.8 |

Additionally, individual miRNA models were analyzed to determine a cutoff resulting in at least 80% sensitivity or at least 80% specificity. These values are presented in Table 3A.

TABLE 3A

Additional Analysis of Individual miRNAs

| ROC model | Cutoff for ~80% Sensitivity ($2^{-\Delta CT}$ normalized expression values) | Cutoff for ~80% Specificity ($2^{-\Delta CT}$ normalized expression values) |
|---|---|---|
| mir-125b | >0.034751697 | >0.087191012 |
| mir-150 | >0.000803 | >0.05414797 |
| mir-342 | >0.109 | >0.0722 |
| mir-451a | >0.469175377 | >0.469175377 |
| mir-3613 | ≤0.00721172 | ≤0.003256935 |
| let-7b | ≤0.0092635 | ≤0.005227312 |

Figure 5:
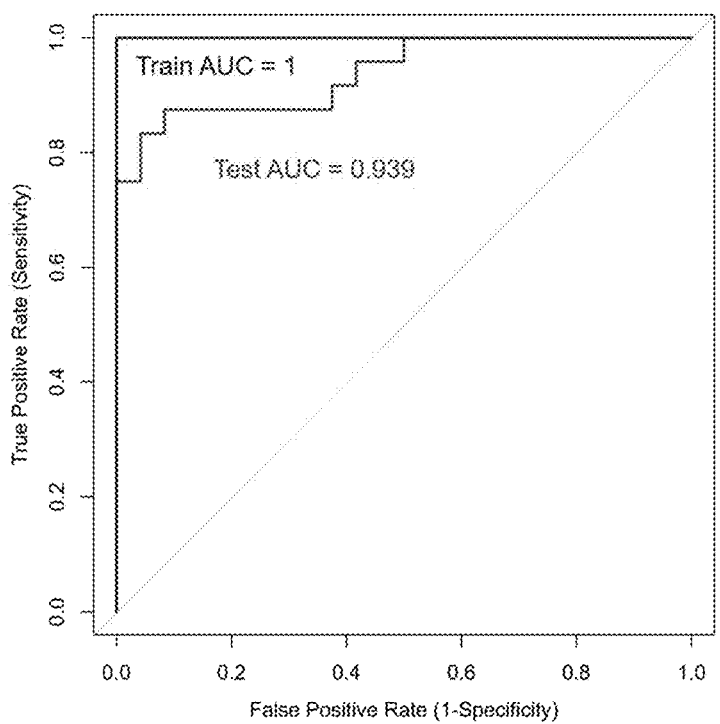
FIG. 5 depicts a receiver operating characteristic (ROC) curve showing performance of the classifier algorithm in an independent data set. Graph shows analysis of the Random Forest model using six miRNA biomarkers (miR-125b-5p, miR-150-5p, miR-342-3p, miR-451a, miR-3613-5p, let-7b). The model was derived in the current (n=100) dataset ("Train") and tested against the retrospective Cosar et al. Fertil Steril. 2016 August; 106(2):402-9. doi: 10.1016/j.fertnstert.2016.04.013 ("Cosar") study (n=48) dataset ("Test").

Example 4.—Multivariate Model-Building and Analysis Based on miRNA Expression in Serum First, the diagnostic performance of the previously reported combination of miR-125b-5p, miR-451a, and miR-3613-5p was assessed (see Cosar et al. *Fertility and sterility.* 2016; 106(2):402-409.). When tested against the current dataset, this combination yielded an AUC score of 0.8. Because the prior study only included women with moderate/severe (Stage III/IV) endometriosis, and the current study included more cases of minimal/mild (Stage I/II) disease, machine-learning based optimization analysis was performed to identify the highest scoring combination of miRNA biomarkers in this more diverse and representative patient population. Using machine learning with a Random Forest approach, a new machine learning model was developed using the six miRNAs. This model was validated in two ways: by random subsampling dividing the total dataset into training and testing subsets, and by testing against an independent dataset (n=48, 24 endometriosis and 24 control subjects). The AUC scores for the model performance in the training and testing datasets are shown in FIG. 5. An AUC of 0.939 for the 6-marker classifier algorithm was attained in an independent validation experiment, after performing an independent re-quantitation of miRNAs from patient samples followed by application of the algorithm.

Example 5.—Analysis of Multivariate Model and Individual miRNA Results From Serum The study of Examples 1-4 was designed to demonstrate the ability of circulating miRNAs to reliably differentiate endometriosis from other gynecologic pathologies, with robust diagnostic performance in an independent test dataset of a diverse (real-world-like) population. In patients surgically confirmed to have endometriosis, significantly lower expression of the serum miRNAs miR-3613-5p and let-7b was found, and significantly higher expression of serum miRNAs miR-125b-5p, miR-150-5p, miR-451a, and miR-342-3p was found, compared to a control group with varied gynecological conditions. The clinical characteristics of the current study population was reflective of real-world patients with endometriosis, including diverse racial demographics, early- and late-stage disease, and presence of hormonal treatments. The control cases also comprised a greater variety of diseases than in our previous study, in which women in the control group were all diagnosed with different types of cysts (dermoid, ovarian, paratubal cysts, and serous or mucinous cystadenoma). Here, fibroids (leiomyomas) were the leading pathology found in the control patients (n=23), with the second most common being absence of abnormal pathology (Table 1). Evaluation of these markers amongst a cohort of patients with varied pelvic pathologies supports the utility of using these markers in a general population to distinguish endometriosis from other conditions.

Assessing the combination of miR-125b-5p, miR-451a, miR-3613-5p using a logistic regression model an AUC of 0.8 was obtained applying this combination to the current data. As this performance is only moderate, the data generated herein was used in a Random Forest machine learning paradigm to build an optimal classifier based on the six miRNAs assessed in subjects herein, and this classifier yielded an AUC of 0.939 when applied to the independent dataset from our previous study (FIG. 5). Since endometriosis is not a life-threatening condition, optimizing the classifier for specificity (avoiding false positives) would help prevent over-diagnosis, and women could be re-tested if symptoms persist. Accordingly, the 6-miRNA random forest model was optimized for specificity by selecting a different cutoff point on the ROC curve, yielding a model with 96% specificity and 83% sensitivity. Alternatively, optimizing values of both sensitivity and specificity to be close to 90% can be achieved using yet a different cutoff on the ROC curve. Higher sensitivity (and a low false negative rate) could be appropriate for use of the biomarker panel as a screening test.

Example 6.—Generation of Trained Algorithm Models Based on Data Derived Herein

To build an improved model for predicting endometriosis, random forest and penalized linear regression approaches were first applied to determine features of importance the multi-mRNA expression data generated in the previous examples.

For this procedure, 1000 replicates were generated, wherein each replicate included a pair of training and a test set. A stratified bootstrapping approach was employed, as stratified bootstrapping keeps the same portion of cases and controls in the bootstrapped training set. For each replicate, a training set was generated using the bootstrapping method (resampling with replacement), and the samples not selected were used as a testing set. The random split was repeated K=1000 times.

For each pair of data sets, random forest (using ntree=500) or penalized linear regression (using alpha levels=0.4 (using elastic-net), 0.7 (using elastic-net), and 1 (using LASSO); and optimal lambda, which is chosen if it includes the least MSE at each alpha level) was applied to the training set. The predicted probability of having disease using the models build from each method was estimated, and the outcome values were dichotomized with a cutoff of 0.5 (50%). Then the computed weighted accuracy measures such as AUC, specificity, sensitivity, and misclassification rate were calculated. The predicted disease status was compared to the true disease status for the testing set and training set. An overall accuracy measure was calculated, which was the sum of the estimated accuracy measure from the training set and the estimated accuracy from the testing set (weighted appropriately).

For each approach (random forest or penalized regression), the means of overall accuracy and error measures were reported over the 1000 replicates. Similarly, importance measures (for random forest) or the number of times each variable was selected out of 1000 (for penalized regression) were reported. These data are reported in Table 4.

TABLE 4

Mean (SD) of overall accuracy measures using Random Forest (RF) or Penalized Regression (PR) approaches

| Approach | Accuracy Measure | Value |
|---|---|---|
| RF | AUC | 0.9327 (sd = 0.0233) |
| RF | Sensitivity | 0.9427 (sd = 0.0346) |
| RF | Specificity | 0.9228 (sd = 0.0412) |
| RF | Misclassification | 0.067 (sd = 0.0232) |
| PR (alpha = 0.4) | AUC | 0.8918 (sd = 0.0198) |
| PR (alpha = 0.4) | Sensitivity | 0.9132 (sd = 0.0319) |
| PR (alpha = 0.4) | Specificity | 0.8704 (sd = 0.0409) |
| PR (alpha = 0.4) | Misclassification | 0.1072 (sd = 0.0195) |
| PR (alpha = 0.7) | AUC | 0.8918 (sd = 0.0198) |
| PR (alpha = 0.7) | Sensitivity | 0.9129 (sd = 0.0319) |
| PR (alpha = 0.7) | Specificity | 0.8707 (sd = 0.041) |
| PR (alpha = 0.7) | Misclassification | 0.1072 (sd = 0.0195) |
| PR (LASSO, alpha = 1) | AUC | 0.8915 (sd = 0.0195) |
| PR (LASSO, alpha = 1) | Sensitivity | 0.9128 (sd = 0.0318) |
| PR (LASSO, alpha = 1) | Specificity | 0.8702 (sd = 0.0405) |
| PR (LASSO, alpha = 1) | Misclassification | 0.1075 (sd = 0.0192) |

TABLE 5

Mean importance measures using Random Forest (RF) approach

| miRNA feature | Mean.Decrease.Accurary | Mean.Decrease.Gini |
|---|---|---|
| miR-342 | 35.8151 | 21.6168 |
| Let-7b | 32.812 | 18.7671 |
| miR-125 | 29.2109 | 17.0781 |
| miR-150 | 25.2763 | 10.6384 |
| miR-3613 | 24.8889 | 12.9522 |
| miR-451a | 18.0184 | 6.719 |

TABLE 6

Non-zero coefficients for Penalized Regression (PR) approach

| Approach | miRNA feature | Counts |
|---|---|---|
| PR (alpha = 0.4) | miR-125 | 1000 |
| PR (alpha = 0.4) | miR-342 | 1000 |
| PR (alpha = 0.4) | miR-3613 | 1000 |
| PR (alpha = 0.4) | miR-451a | 1000 |
| PR (alpha = 0.4) | Let-7b | 1000 |
| PR (alpha = 0.4) | miR-150 | 995 |
| PR (alpha = 0.7) | miR-125 | 1000 |
| PR (alpha = 0.7) | miR-342 | 1000 |
| PR (alpha = 0.7) | miR-3613 | 1000 |
| PR (alpha = 0.7) | miR-451a | 1000 |
| PR (alpha = 0.7) | Let-7b | 1000 |
| PR (alpha = 0.7) | miR-150 | 981 |
| PR (LASSO, alpha = 1) | miR-342 | 1000 |
| PR (LASSO, alpha = 1) | miR451a | 1000 |
| PR (LASSO, alpha = 1) | Let-7b | 1000 |
| PR (LASSO, alpha = 1) | miR-125 | 999 |
| PR (LASSO, alpha = 1) | miR-3613 | 999 |
| PR (LASSO, alpha = 1) | miR-150 | 956 |

Based on this data, logistic regression and random forest models were built using various numbers of markers selected using RF importance ranking from the model building step above. These models were then validated on the retrospective data from Cosar et al. *Fertility and sterility.* 2016; 106(2):402-409. The data are presented in Table 7 and Table 8.

TABLE 7

Comparison of Models based on Retrospective data generated herein using RF

| miRNA features by importance ranking | AUC | Sensitivity | Specificity | Misclassification |
|---|---|---|---|---|
| miR-342 | 0.8411 | 0.7083 | 0.875 | 0.2083 |
| miR-342, let-7b | 0.7839 | 0.5833 | 0.75 | 0.3333 |
| miR-342, let-7b, miR-125b | 0.9288 | 0.8333 | 0.875 | 0.1458 |
| miR-342, let-7b, miR-125b, miR-150 | 0.9271 | 0.8333 | 0.875 | 0.1458 |
| miR-342, let-7b, miR-125b, miR-150, miR-3613 | 0.9392 | 0.875 | 0.875 | 0.125 |
| miR-125b, miR-451a, miR-3613 | 0.9965 | 0.9583 | 0.9583 | 0.0417 |
| Let-7b, miR-125b, miR-150 | 0.8368 | 0.625 | 0.7083 | 0.3333 |
| miR-125b, miR-451a, miR-3613, miR-150 | 0.9479 | 0.9167 | 0.9167 | 0.0833 |

TABLE 8

Comparison of Models based on Bootstrapped Retrospective data using Logistic Regression (LR)

| miRNA features by importance ranking | AUC | Sensitivity | Specificity | Misclassification |
|---|---|---|---|---|
| miR-342 | 0.7882 | 0.875 | 0.7917 | 0.1667 |
| miR-342, let-7b | 0.7569 | 0.625 | 0.7917 | 0.2917 |
| miR-342, let-7b, miR-125b | 0.8082 | 0.6667 | 0.7917 | 0.2708 |
| miR-342, let-7b, miR-125b, miR-150 | 0.803 | 0.6667 | 0.7917 | 0.2708 |
| miR-342, let-7b, miR-125b, miR-150, miR-3613 | 0.8273 | 0.75 | 0.7917 | 0.2292 |
| miR-125b, miR-451a, miR-3613 | 0.9167 | 0.9167 | 0.875 | 0.1042 |
| Let-7b, miR-125b, miR-150 | 0.7795 | 0.625 | 0.75 | 0.3125 |
| miR-125b, miR-451a, miR-3613, miR-150 | 0.9236 | 0.9167 | 0.875 | 0.1042 |

Based on the data in Tables 7 and 8, random forest was determined to be the superior trained-algorithm approach to classifying data from the current study (as it produced superior results for all the miRNA feature combinations).

Figure 7:
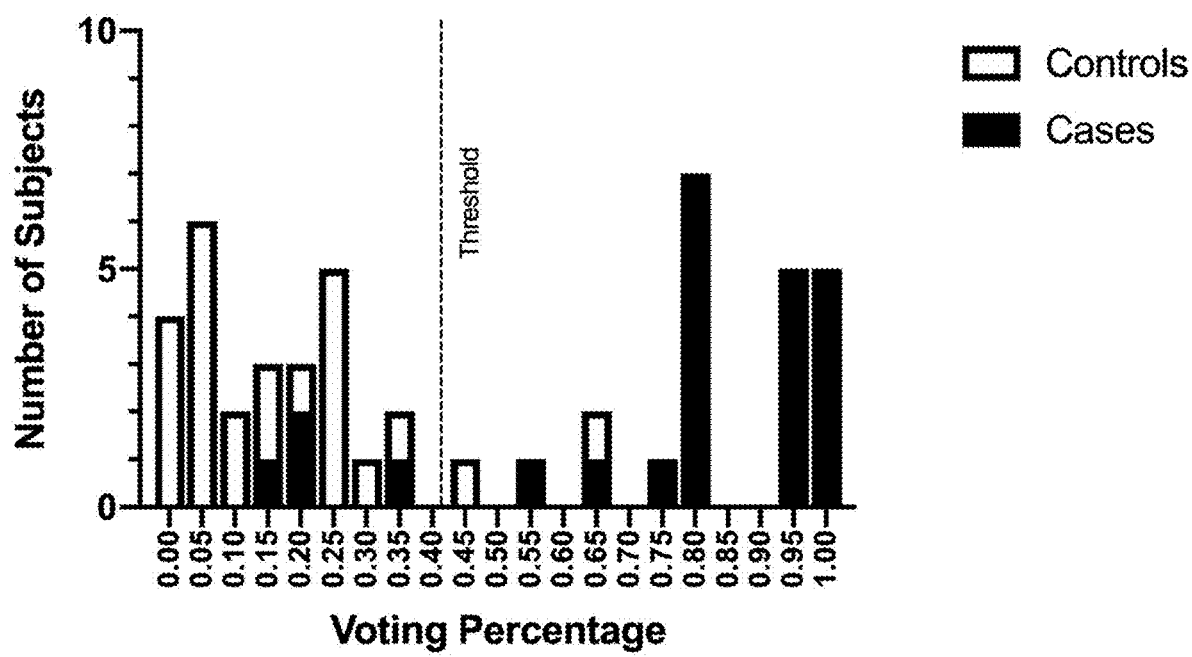
FIG. 7 depicts a histogram the distribution of voting percentages from the RF model in the Retrospective data set (Cosar); black bars indicate subjects with surgically defined endometriosis, white bars subjects without endometriosis. Using a diagnostic threshold (cut-off) of 43%, shown by the dashed vertical line, results in a 96% specificity and 83% sensitivity for the RF model in this data set.

Accordingly, the random forest learning approach was applied to either this data set or data sets from previous studies, and cutoffs were determined to optimize performance of the models. As an example demonstration, FIG. 7 shows a histogram where the distribution of voting percentages from the RF model in the Retrospective data set (Cosar); black bars indicate subjects with surgically defined endometriosis, white bars subjects without endometriosis. Using a diagnostic threshold (cut-off) of 43%, shown by the dashed vertical line, results in a 96% specificity and 83% sensitivity for the RF model in this data set.

We extended this analysis to determine if classifiers built from all the biomarkers used in models herein (miR-125b, miR-451a, miR-3613, miR-150, miR-342, and let-7b) could be generalizeable to a variety of different samples.

TABLE 9

Importance Measures of miRNAs Performance of RF Models with Given Importance Measures and Feature Rankings on Various Data Sets

| Improved Saliva data set model (PCT/US2017/049284), n = 77 (A) | Improved Serum data set model (Combined Cosar et al. + Current study) n = 148 (B) | Improved RF model Current Study (Prospective data) n = 100 (C) | Improved Cosar et al. model (Retrospective data) n = 48 (D) |
|---|---|---|---|
| miR.125b (imp.measure = 25.8126) | miR.342 (imp.measure = 33.553) | miR.342 (imp.measure = 32.1419) | miR.125b (imp.measure = 23.5962) |
| miR.let.7b (imp.measure = 23.8138) | miR.125b (imp.measure = 25.4793) | miR.451a (imp.measure = 20.7367) | miR.3613 (imp.measure = 12.816) |
| miR.3613 (imp.measure = 20.5754) | miR.451a (imp.measure = 24.5819) | miR.3613 (imp.measure = 17.5145) | miR.451a (imp.measure = 11.9758) |
| miR.150 (imp.measure = 15.5134) | miR.3613 (imp.measure = 20.3705) | miR.125b (imp.measure = 15.6668) | miR.150 (imp.measure = 10.8909) |
| miR.342 (imp.measure = 13.7667) | miR.150 (imp.measure = 16.4008) | let.7b (imp.measure = 14.9393) | miR.342 (imp.measure = 10.1744) |
| miR.451a (imp.measure = 10.647) | let.7b (imp.measure = 15.1521) | miR.150 (imp.measure = 14.8499) | miR.let.7b (imp.measure = 5.1379) |

TABLE 10

Performance of RF Models in Table 9

| Study/model | AUC | Sensitivity | Specificity | Misclassification |
|---|---|---|---|---|
| Improved Saliva data set model (PCT/US2017/049284), n = 77 | 0.9386 (sd = 0.0331) | 0.9247 (sd = 0.0606) | 0.9524 (sd = 0.0442) | 0.0603 (sd = 0.0321) |
| Improved Serum data set model (Combined Cosar et al. + Current study) n = 148 | 0.9345 (sd = 0.0237) | 0.9623 (sd = 0.0276) | 0.9068 (sd = 0.049) | 0.0624 (sd = 0.022) |
| Improved RF model Current Study (Prospective data) n = 100 | 0.9363 (sd = 0.0299) | 0.969 (sd = 0.0292) | 0.9036 (sd = 0.0595) | 0.0582 (sd = 0.0267) |
| Improved Cosar et al. model (Retrospective data) n = 48 | 0.9696 (sd = 0.0265) | 0.9696 (sd = 0.0383) | 0.9696 (sd = 0.0505) | 0.0306 (sd = 0.0268) |

Importantly, the six-marker model (D) demonstrated high performance (greater than 0.93 AUC) in all data sets.

Example 7.—Detection, Diagnosis and Treatment of Endometriosis

A blood, blood plasma, blood serum, menstrual blood, menstrual effluent, urine, or saliva sample is taken from a female patient with suspicion of endometriosis. The quantity of a microRNA associated with endometriosis (for example, miR-125b, miR-451a, miR-3613, miR-150, miR-342, and let-7b) is then determined in the sample, and any of the trained algorithm classifiers used herein are utilized to detect endometriosis. If endometriosis is detected, the patient is treated with a therapeutically effective dose of a GnRH antagonist or agonist therapy (e.g., Elagolix). The compound causes a reduction in the symptoms of endometriosis. After one month of treatment, six months of treatment, and one year of treatment, the patient is assessed for levels of a microRNA signature associated with endometriosis. If the microRNA signature associated with endometriosis indicates the presence of endometriosis, the dose of the GnRH agonist or antagonist therapy (e.g., Elagolix) is adjusted upward, and the treatment/testing process is repeated until biomarkers indicate the absence of endometriosis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting and treating endometriosis in a female subject, comprising:
   (a) detecting in a bodily fluid sample from the female subject an expression profile of a panel of miRNAs associated with endometriosis, wherein the panel of miRNAs associated with endometriosis comprises miR-342 and at least one miRNA selected from the group consisting of miR-150, miR-3613, miR-451a, and miR-125b;
   (b) applying a machine learning algorithm to the expression profile of the panel of miRNAs associated with endometriosis, wherein the machine learning algorithm has importance measures assigned to miRNA features based on miRNA expression data from a plurality of endometriosis samples, and wherein:
   the machine learning algorithm assigns an importance measure to miR-342 and to at least one miRNA selected from the group consisting of miR-150, miR-3613, miR-451a, and miR-125b; wherein the importance measure assigned to miR-342 is greater than the importance measure assigned to the at least one miRNA selected from the group consisting of miR-150, miR-3613, miR-451a, and miR-125b;
   (c) using the machine learning algorithm to detect a presence of endometriosis in the female subject; and
   (d) treating the female subject with a treatment for endometriosis when the machine learning algorithm detects the presence of endometriosis in the female subject, wherein the treatment for endometriosis comprises at least one treatment selected from the group consisting of hormonal treatment, surgery, laparoscopic surgery, a statin, a non-steroidal anti-inflammatory drug (NSAID), an oral contraceptive, a progestin, a gonadotrophin releasing (GnRH) agonist, a GnRH antagonist, an androgen, an antiprogesterone, a selective estrogen receptor modulator (SERM), a selective progesterone receptor modulator (SPRM), atorvastatin, cerivastatin, fluvastatin, lovastatin, mevastatin, pitavastatin, pravastatin, rosuvastatin, simvastatin, paracetamol, a COX-2 inhibitor, and aspirin.

2. The method of claim 1, wherein the importance measure assigned to miR-342 is greater than the importance measure assigned to at least two miRNAs selected from the group consisting of: miR-150, miR-3613, miR-451a, let-7b, and miR-125b.

3. The method of claim 1, wherein the bodily fluid sample is a cell-free sample.

4. The method of claim 1, wherein the bodily fluid sample is a blood sample, a plasma sample, a saliva sample, or a serum sample.

5. The method of claim 1, wherein the machine learning algorithm assigns an importance measure to miR-342, miR-150, miR-3613, miR-451a, let-7b, and miR-125b wherein the importance measure ranking from highest to lowest is miR-342, miR-451a, miR-3613, miR-125b, let-7b, and miR-150.

6. The method of claim 1, wherein the machine learning algorithm is a random forest algorithm, k-nearest-neighbors algorithm (KNN), support vector machine (SVM), or Naive Bayes.

7. The method of claim 1, wherein the machine learning algorithm is a random forest algorithm.

8. The method of claim 1, wherein the method detects endometriosis in a population of women with a specificity of greater than 80%.

9. The method of claim 8, wherein the population of women is premenopausal women.

10. The method of claim 8, wherein the population of women comprises women with leiomyomas, cystadenomas, chronic pelvic infections, teratomas, endometriomas, or paratubal cysts.

11. The method of claim 8, wherein the population of women comprises women with Stage I/II endometriosis.

12. The method of claim 8, wherein the population of women comprises women with Stage III/IV endometriosis or women with all four stages of endometriosis.

13. The method of claim 8, wherein the population of women comprises women having received hormone therapy within 3 months of the date on which the bodily fluid sample was obtained or women at any phase of their menstrual cycle.

14. The method of claim 8, wherein the population of women comprises a cohort comprising at least 100 women.

15. The method of claim 1, wherein the machine learning algorithm is trained on expression data from at least 100 samples.

16. The method of claim 1, wherein the machine learning algorithm is trained on a population of women comprising women having stages I-IV endometriosis.

17. The method of claim 1, wherein the method has an AUC for detecting endometriosis of greater than 0.85 in a population of women.

18. The method of claim 1, wherein the endometriosis treatment comprises surgery or laparoscopic surgery.

19. The method of claim 1, wherein the bodily fluid sample is a plasma sample or serum sample.

20. A method of detecting and treating endometriosis condition in a female subject, comprising:
    (a) detecting in a bodily fluid sample from the female subject an expression profile of a panel of miRNAs associated with endometriosis, wherein the panel of miRNAs associated with endometriosis comprises miR451-a and at least one miRNA selected from the group consisting of miR-3613, miR-125, and let-7b;
    (b) applying a machine learning algorithm to the expression profile of the panel of miRNAs associated with endometriosis, wherein the machine learning algorithm has importance measures assigned to miRNA features based on miRNA expression data from a plurality of endometriosis samples, and wherein the machine learning algorithm assigns an importance measure to miR-451a and to the at least one miRNA selected from the group consisting of miR-3613, miR-125, and let-7b, wherein the importance measure assigned to miR-451a is greater than the importance measure assigned to the at least one miRNA selected from the group consisting of miR-3613, miR-125, and let-7b;
    (c) using the machine learning algorithm to detect a presence of endometriosis in the female subject; and
    (d) treating the female subject with a treatment for endometriosis when the machine learning algorithm detects the presence of endometriosis in the female subject wherein the treatment for endometriosis comprises a hormonal treatment, surgery, laparoscopic surgery, a statin, a non-steroidal anti-inflammatory drug (NSAID), an oral contraceptive, a progestin, a gonadotrophin releasing (GnRH) agonist, a GnRH antagonist, an androgen, an antiprogesterone, a selective estrogen receptor modulator (SERM), a selective progesterone receptor modulator (SPRM), atorvastatin, cerivastatin, fluvastatin, lovastatin, mevastatin, pitavastatin, pravastatin, rosuvastatin, simvastatin, paracetamol, a COX-2 inhibitor, or aspirin.

21. The method of claim 20, wherein the bodily fluid sample is a blood sample, a plasma sample, a saliva sample, or a serum sample.

22. The method of claim 20, wherein the panel of miRNAs associated with endometriosis comprises at least two miRNA selected from the group consisting of miR-3613, miR-125, and let-7b.

23. The method of claim 20, wherein the machine learning algorithm is a random forest algorithm, k-nearest-neighbors algorithm (KNN), support vector machine (SVM), or Naive Bayes.

24. The method of claim 20, wherein the machine learning algorithm is a random forest algorithm.

25. The method of claim 20, wherein the method detects endometriosis in a population of women with a specificity of greater than 80%.

26. The method of claim 25, wherein the wherein the population of women comprises a cohort comprising at least 100 women.

27. The method of claim 20, wherein the machine learning algorithm is trained on a population of women comprising women having stages I-IV endometriosis.

28. The method of claim 20, wherein the method has an AUC for detecting endometriosis of greater than 0.85 in a population of women.

29. The method of claim 20, wherein the endometriosis treatment comprises surgery or laparoscopic surgery.

30. The method of claim 20, wherein the bodily fluid sample is a plasma sample or serum sample.

* * * * *

```
                        SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgaggtagta ggttgtgtgg tt                                           22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccctgagac cctaacttgt ga                                           22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctcccaacc cttgtaccag tg                                           22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctcacacag aaatcgcacc cgt                                          23
```

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
aaaccgttac cattactgag tt                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tgttgtactt tttttttgt tc                                               22

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ctcgcttcgg cagcaca                                                    17

<210> SEQ ID NO 8
<211> LENGTH: 22
<212> TYPE: RNA
<213> ORGANISM: Homo sapiens

<400> SEQUENCE: 8
ugagguagua gguugugugg uu                                              22

<210> SEQ ID NO 9
<211> LENGTH: 22
<212> TYPE: RNA
<213> ORGANISM: Homo sapiens

<400> SEQUENCE: 9
ucccugagac ccuaacuugu ga                                              22

<210> SEQ ID NO 10
<211> LENGTH: 22
<212> TYPE: RNA
<213> ORGANISM: Homo sapiens

<400> SEQUENCE: 10
ucucccaacc cuuguaccag ug                                              22

<210> SEQ ID NO 11
<211> LENGTH: 23
<212> TYPE: RNA
<213> ORGANISM: Homo sapiens

<400> SEQUENCE: 11
ucucacacag aaaucgcacc cgu                                             23

```
<210> SEQ ID NO 12
<211> LENGTH: 22
<212> TYPE: RNA
<213> ORGANISM: Homo sapiens

<400> SEQUENCE: 12
aaaccguuac cauuacugag uu                                              22

<210> SEQ ID NO 13
<211> LENGTH: 22
<212> TYPE: RNA
<213> ORGANISM: Homo sapiens

<400> SEQUENCE: 13
uguuguacuu uuuuuuugu uc                                               22

<210> SEQ ID NO 14
<211> LENGTH: 17
<212> TYPE: RNA
<213> ORGANISM: Homo sapiens

<400> SEQUENCE: 14
cucgcuucgg cagcaca                                                    17
```